United States Patent
Boehm et al.

(10) Patent No.: US 10,016,758 B2
(45) Date of Patent: Jul. 10, 2018

(54) ROTATABLE CARTRIDGE FOR ANALYZING A BIOLOGICAL SAMPLE

(71) Applicant: Roche Diagnostics Operations, Inc., Indianapolis, IN (US)

(72) Inventors: Christoph Boehm, Viernheim (DE); Sascha Lutz, Neustadt (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 15/352,689

(22) Filed: Nov. 16, 2016

(65) Prior Publication Data
US 2017/0095813 A1    Apr. 6, 2017

Related U.S. Application Data

(63) Continuation of application No. PCT/EP2015/054534, filed on Mar. 4, 2015.

(30) Foreign Application Priority Data

Jun. 6, 2014 (EP) .................................... 14171425

(51) Int. Cl.
    G01N 1/38 (2006.01)
    G01N 35/00 (2006.01)
    (Continued)

(52) U.S. Cl.
    CPC ..... B01L 3/50273 (2013.01); B01L 3/502738 (2013.01); G01N 1/38 (2013.01);
    (Continued)

(58) Field of Classification Search
    CPC .............. B01L 3/00; G01N 1/38; G01N 35/00
    (Continued)

(56) References Cited

U.S. PATENT DOCUMENTS 4,284,602 A * 8/1981 Kelton ............... G01N 21/07
                                                    356/246
4,469,793 A * 9/1984 Guigan ............... B04B 5/0407
                                                    422/503
(Continued)

FOREIGN PATENT DOCUMENTS

EP         2302396 A1     3/2011

OTHER PUBLICATIONS

Kim et al., "Flow-enhanced electrochemical immunosensors on centrifugal microfluidic platforms", Lab on a Chip 13.18 2013; pp. 3747-3754, doi: 10.1039/c3lc50374g.
(Continued)

*Primary Examiner* — Arlen Soderquist
(74) *Attorney, Agent, or Firm* — Dinsmore & Shohl, LLP

(57) ABSTRACT

An automatic analyzer cartridge spinnable around a rotational axis has a fluid chamber for receiving a fluid, an aliquoting chamber, a duct connecting the fluid chamber and the aliquoting chamber, a downstream fluidic element, a siphon for siphoning the fluid from the aliquoting chamber to the downstream fluidic element, a fluidic structure for processing a biological sample into the processed biological sample, and a measurement structure for enabling measurement of the processed biological sample. The siphon has a siphon entrance in the aliquoting chamber and a siphon exit in the downstream fluidic element, wherein the siphon has a bend, wherein the bend is the portion of the siphon closest to the rotational axis, wherein the siphon entrance starts at the bend, wherein the siphon entrance extends to a lower portion of the aliquoting chamber. This enables multiple aliquots of fluid to be removed from the aliquoting chamber by the siphon.

16 Claims, 11 Drawing Sheets

(51) Int. Cl.
*B01L 3/00* (2006.01)
*G01N 35/10* (2006.01)

(52) U.S. Cl.
CPC ... *G01N 35/00069* (2013.01); *G01N 35/1016* (2013.01); *B01L 2200/0684* (2013.01); *B01L 2200/10* (2013.01); *B01L 2300/044* (2013.01); *B01L 2300/0672* (2013.01); *B01L 2300/0803* (2013.01); *B01L 2300/087* (2013.01); *B01L 2400/0406* (2013.01); *B01L 2400/0409* (2013.01); *B01L 2400/0688* (2013.01); *B01L 2400/0694* (2013.01); *G01N 2035/00257* (2013.01); *G01N 2035/1032* (2013.01)

(58) Field of Classification Search
USPC .............................................. 422/72; 436/45
See application file for complete search history.

(56) References Cited

U.S. PATENT DOCUMENTS

| | | | | |
|---|---|---|---|---|
| 4,894,204 A * | 1/1990 | Cornut | ................... | G01N 21/07 422/72 |
| 5,061,381 A * | 10/1991 | Burd | ...................... | G01N 21/07 210/198.1 |
| 5,089,417 A * | 2/1992 | Wogoman | ............. | B04B 5/0407 210/787 |
| 5,160,702 A * | 11/1992 | Kopf-Sill | ............... | G01N 21/07 422/72 |
| 5,173,193 A * | 12/1992 | Schembri | ............... | G01N 21/07 210/198.1 |
| 5,173,262 A * | 12/1992 | Burtis | .................... | G01N 21/07 422/72 |
| 5,186,844 A * | 2/1993 | Burd | ...................... | G01N 21/07 422/72 |
| 5,304,348 A * | 4/1994 | Burd | ...................... | G01N 21/07 422/72 |
| 5,591,643 A * | 1/1997 | Schembri | ............... | G01N 21/07 210/198.1 |
| 6,299,839 B1 * | 10/2001 | Karunaratne | ....... | B01F 13/0818 422/72 |
| 7,371,330 B2 * | 5/2008 | Ducree | ............ | B01L 3/502753 422/72 |
| 7,727,472 B2 * | 6/2010 | Nagaoka | ................ | G01N 21/07 422/50 |
| 7,938,030 B2 * | 5/2011 | Saiki | ..................... | B01L 3/5027 422/503 |
| 7,951,332 B2 * | 5/2011 | Cho | ................... | B01L 3/50273 422/502 |
| 7,972,577 B2 * | 7/2011 | Horiike | ............ | B01L 3/502746 422/50 |
| 8,048,387 B2 * | 11/2011 | Lee | .................... | B01L 3/50273 422/502 |
| 8,114,351 B2 | 2/2012 | Degenhardt | | |
| 8,440,147 B2 * | 5/2013 | Garcia Da Fonseca | ............. | B01L 3/50273 422/50 |
| 8,470,588 B2 | 6/2013 | Boehm et al. | | |
| 8,796,029 B2 * | 8/2014 | Chung | ............. | B01L 3/502738 422/64 |
| 8,911,684 B2 * | 12/2014 | Augstein | ............... | B01F 1/0027 422/50 |
| 8,956,580 B2 * | 2/2015 | Lai | ......................... | B01L 3/508 422/415 |
| 9,012,228 B2 * | 4/2015 | Kim | ..................... | G01N 33/491 422/502 |
| 9,151,750 B2 * | 10/2015 | Boehm | ............. | B01L 3/502753 |
| 9,186,671 B2 * | 11/2015 | Augstein | .......... | B01L 3/502738 |
| 9,221,051 B2 * | 12/2015 | Boehm | ............. | B01L 3/502738 |
| 9,417,164 B2 * | 8/2016 | Boehm | ............. | B01F 1/0022 |
| 2002/0106786 A1 * | 8/2002 | Carvalho | ............. | B01F 5/0647 435/287.3 |
| 2003/0053934 A1 * | 3/2003 | Andersson | ............ | B01F 5/0646 422/72 |
| 2008/0035579 A1 * | 2/2008 | Lee | .................... | B01L 3/502761 210/695 |
| 2008/0058991 A1 * | 3/2008 | Lee | ........................ | B01L 3/5027 700/266 |
| 2008/0108120 A1 * | 5/2008 | Cho | .................... | B01F 13/0059 435/173.7 |
| 2009/0053108 A1 * | 2/2009 | Cho | .................. | B01L 3/502753 422/72 |
| 2009/0155925 A1 * | 6/2009 | Boehm | ............... | B01L 3/50273 436/174 |
| 2009/0169430 A1 * | 7/2009 | Yamamoto | .......... | B01L 3/50273 422/72 |
| 2009/0191643 A1 * | 7/2009 | Boehm | ............. | B01L 3/502738 436/164 |
| 2009/0193913 A1 * | 8/2009 | Saiki | ..................... | B01L 3/5027 73/864.72 |
| 2009/0246082 A1 | 10/2009 | Saiki et al. | | |
| 2009/0317896 A1 * | 12/2009 | Yoo | ................... | B01L 3/502738 422/72 |
| 2010/0158757 A1 * | 6/2010 | Horiike | ............ | B01L 3/502746 422/72 |
| 2011/0053202 A1 * | 3/2011 | Parng | ................ | B01L 3/502746 435/29 |
| 2011/0201101 A1 * | 8/2011 | Lee | ..................... | B01L 3/50273 435/288.7 |
| 2011/0263030 A1 * | 10/2011 | Kim | .................... | B01L 3/50273 436/45 |
| 2012/0301371 A1 * | 11/2012 | Augstein | ................ | B01F 1/0027 422/502 |
| 2013/0004964 A1 * | 1/2013 | Boehm | ............. | B01L 3/502753 435/7.4 |
| 2013/0196447 A1 * | 8/2013 | Boehm | ................ | B01F 1/0022 436/166 |
| 2013/0236376 A1 * | 9/2013 | Augstein | ............ | B01L 3/502738 422/506 |
| 2013/0243664 A1 * | 9/2013 | Boehm | ............. | B01L 3/502738 422/504 |
| 2014/0309555 A1 * | 10/2014 | Gelfand | ........... | A61B 5/150305 600/583 |
| 2016/0320274 A1 * | 11/2016 | Boehm | ................ | B01F 1/0022 |
| 2017/0095811 A1 * | 4/2017 | Boehm | ............ | G01N 35/00069 |
| 2017/0095812 A1 * | 4/2017 | Boehm | ............. | B01L 3/50273 |
| 2017/0095814 A1 * | 4/2017 | Boehm | ............. | B01L 3/50273 |

OTHER PUBLICATIONS

Martinez-Duarte et al., "The integration of 3D carbon-electrode dielectrophoresis on a CD-like centrifugal microfluidic platform", Lab on a Chip 10.8, 2010; pp. 1030-1043, doi: 10.1039/B925456K.

* cited by examiner

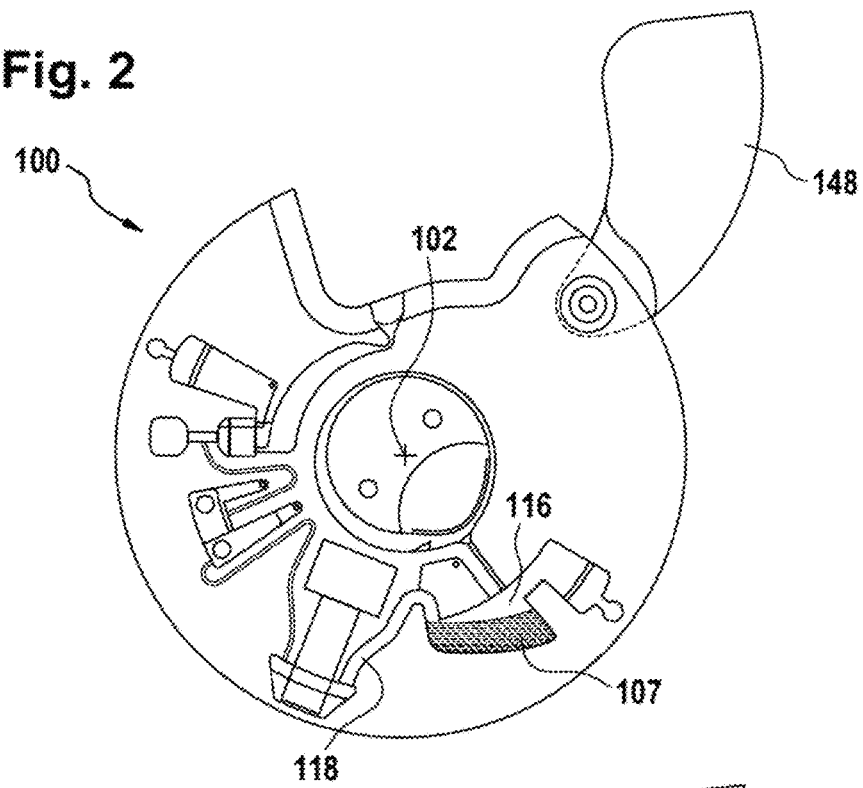
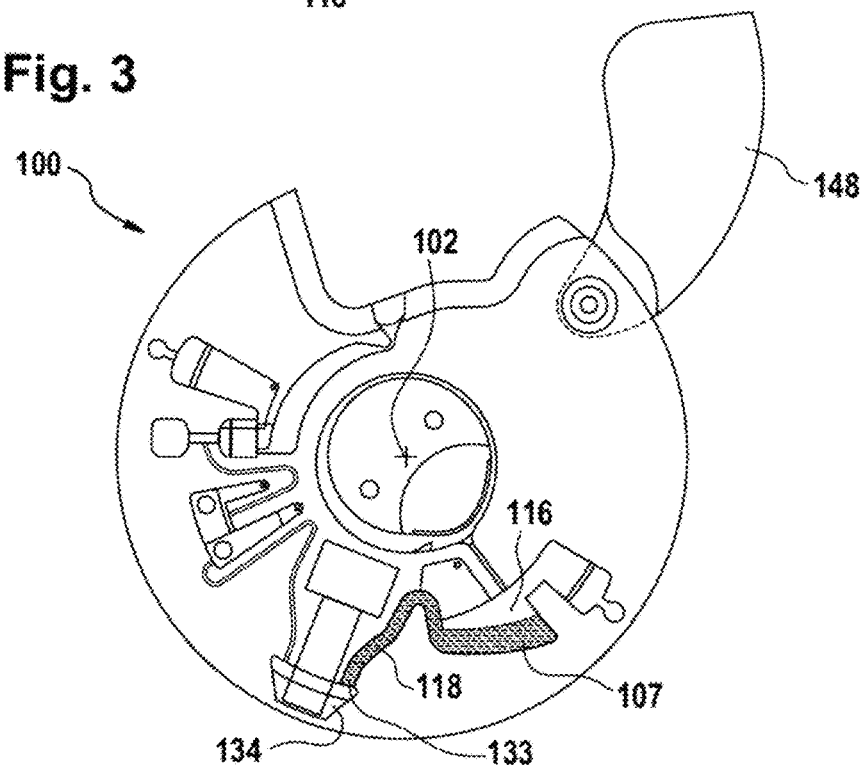

Fig. 13
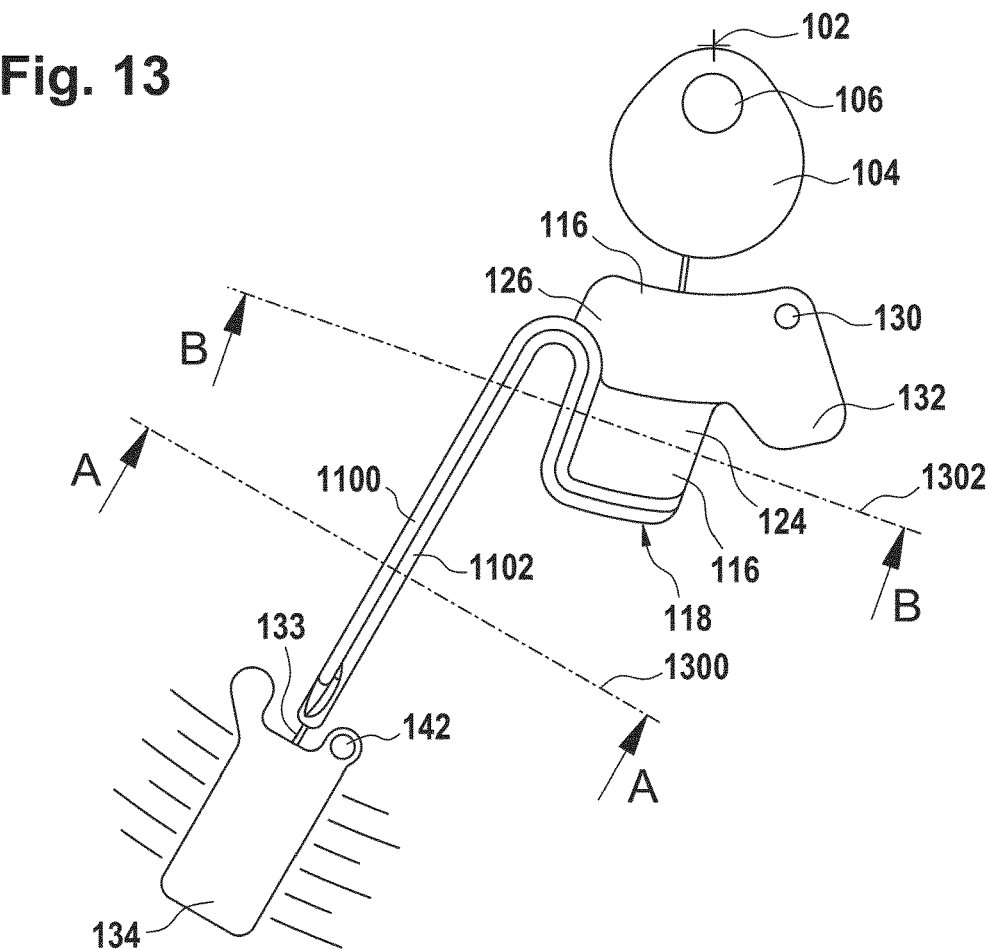
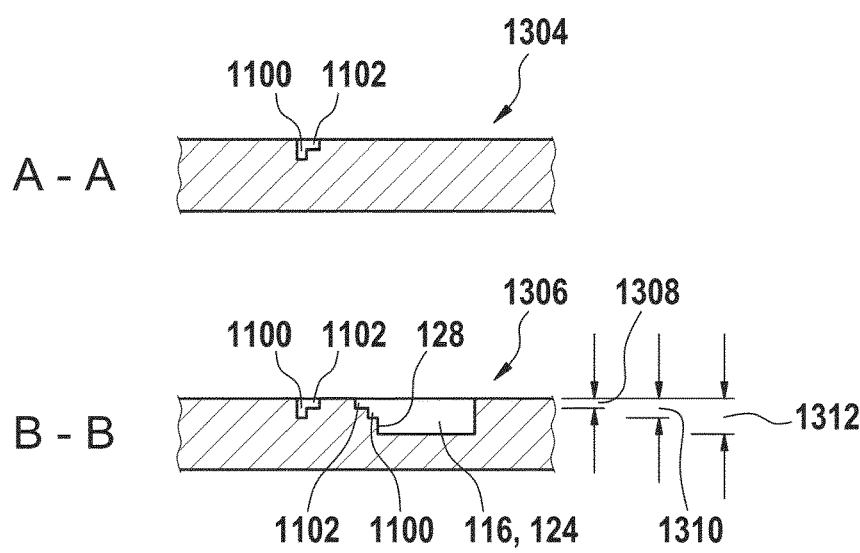

ROTATABLE CARTRIDGE FOR ANALYZING A BIOLOGICAL SAMPLE

CROSS-REFERENCE TO RELATED APPLICATIONS

This application is a continuation of International Application No. PCT/EP2015/054534, filed Mar. 4, 2015, which claims priority to European patent application No. EP14171425.3, filed Jun. 6, 2014.

TECHNICAL FIELD

The inventive embodiments disclosed relate to analytical test devices for biological samples, in particular to the design and use of rotatable cartridges for performing a measurement on of a biological sample.

BACKGROUND AND RELATED ART

Two classes of analysis systems are known in the field of medical analysis: wet analysis systems, and dry-chemical analysis systems. Wet analysis systems, which essentially operate using "wet reagents" (liquid reagents), perform an analysis via a number of required step such as, for example, providing a sample and a reagent into a reagent vessel, mixing the sample and reagent together in the reagent vessel, and measuring and analyzing the mixture for a measurement variable characteristic to provide a desired analytical result (analysis result). Such steps are often performed using technically complex, large, line-operated analysis instruments, which allow required manifold movements of participating elements. This class of analysis system is typically used in large medical-analytic laboratories.

On the other hand, dry-chemical analysis systems operate using "dry reagents" which are typically integrated in a test element and implemented as a "test strip", for example. When these dry-chemical analysis systems are used, the liquid sample dissolves the reagents in the test element, and the reaction of sample and dissolved reagent results in a change of a measurement variable, which can be measured on the test element itself. Above all, optically analyzable (in particular colorimetric) analysis systems are typical in this class, in which the measurement variable is a color change or other optically measurable variable. Electrochemical systems are also typical in this class, in which an electrical measurement variable characteristic for the analysis, in particular an electrical current upon application of a defined voltage, can be measured in a measuring zone of the test element using electrodes provided in the measuring zone.

The analysis instruments of the dry-chemical analysis systems are usually compact, and some of them are portable and battery-operated. The systems are used for decentralized analysis, for example, at resident physicians, on the wards of the hospitals, and in so-called "home monitoring" during the monitoring of medical-analytic parameters by the patient himself (in particular blood glucose analysis by diabetics or coagulation status by warfarin patients).

In wet analysis systems, the high-performance analysis instruments allow the performance of more complex multi-step reaction sequences ("test protocols"). For example, immunochemical analyses often require a multistep reaction sequence, in which a "bound/free separation" (hereafter "b/f separation"), i.e., a separation of a bound phase and a free phase, is necessary. According to one test protocol, for example, the probe can first be transported through a porous solid matrix, which contains a specific binding reagent for the analyte. A marking reagent can subsequently be caused to flow through the porous matrix, to mark the bound analyte and allow its detection. To achieve precise analysis, a washing step must previously be performed, in which unbound marking reagent is completely removed. Numerous test protocols are known for determining manifold analytes, which differ in manifold ways, but which share the feature that they require complex handling having multiple reaction steps, in particular also a b/f separation possibly being necessary.

Test strips and similar analysis elements normally do not allow controlled multistep reaction sequences. Test elements similar to test strips are known, which allow further functions, such as the separation of red blood cells from whole blood, in addition to supplying reagents in dried form. However, they normally do not allow precise control of the time sequence of individual reaction steps. Wet-chemical laboratory systems offer these capabilities, but are too large, too costly, and too complex to handle for many applications.

To close these gaps, analysis systems have been suggested which operate using test elements which are implemented in such a manner that at least one externally controlled (i.e., using an element outside the test element itself) liquid transport step occurs therein ("controllable test elements"). The external control can be based on the application of pressure differences (overpressure or low-pressure) or on the change of force actions (e.g., change of the action direction of gravity by attitude change of the test element or by acceleration forces). The external control is especially frequently performed by centrifugal forces, which act on a rotating test element as a function of the velocity of the rotation.

Analysis systems having controllable test elements are known and typically have a housing, which comprises a dimensionally-stable plastic material, and a sample analysis channel enclosed by the housing, which often comprises a sequence of multiple channel sections and chambers expanded in comparison to the channel sections lying between them. The structure of the sample analysis channel having its channel sections and chambers is defined by profiling of the plastic parts. This profiling is able to be generated by injection molding techniques or hot stamping. Microstructures, which are generated by lithography methods, are increasingly being used.

Analysis systems having controllable test elements allow the miniaturization of tests which have only been able to be performed using large laboratory systems. In addition, they allow the parallelization of procedures by repeated application of identical structures for the parallel processing of similar analyses from one sample and/or identical analyses from different samples. It is a further advantage that the test elements can typically be produced using established production methods and that they can also be measured and analyzed using known analysis methods. Known methods and products can also be employed in the chemical and biochemical components of such test elements.

In spite of these advantages, there is a further need for improvement. In particular, analysis systems which operate using controllable test elements are still too large. The most compact dimensions possible are of great practical significance for many intended applications.

U.S. Pat. No. 8,114,351 B2 discloses an analysis system for the analysis of a body fluid sample for an analyte. The analysis system provides a test element and an analysis instrument having a dosing station and a measurement station. The test element has a housing an (at least) one sample analysis channel enclosed by the housing. The test element is rotatable around an axis of rotation which extends through the test element.

U.S. Pat. No. 8,470,588 B2 discloses a test element and a method for detecting an analyte. The test element is essentially disk shaped and flat, and can be rotated about a preferably central axis which is perpendicular to the plane of the disk shaped test element.

Kim, Tae-Hyeong, et al. "Flow-enhanced electrochemical immunosensors on centrifugal microfluidic platforms." Lab on a Chip 13.18 (2013): 3747-3754, doi:10.1039/c3lc50374g, (hereafter "Kim et. al.") discloses a fully integrated centrifugal microfluidic device with features for target antigen capture from biological samples, via a bead-based enzyme-linked immune-sorbent assay, and flow-enhanced electrochemical detection. This is integrated into a Centrifugal microfluidic discs, also known as "lab-on-a-disc" or microfluidic CDs.

Martinez-Duarte, Rodrigo, et al. "The integration of 3D carbon-electrode dielectrophoresis on a CD-like centrifugal microfluidic platform." Lab on a Chip 10.8 (2010): 1030-1043, doi:10.1039/B925456K, (hereafter "Martinez-Duarte et. al.") discloses a dielectrophoresis (DEP)-assisted filter with a compact disk (CD)-based centrifugal platform. 3D carbon electrodes are fabricated using the C-MEMS technique and are used to implement a DEP-enabled active filter to trap particles of interest.

European Patent application EP 2 302 396 A1 discloses an analyzing device includes: an operation cavity that is adjacent to a first reserving cavity retaining a sample liquid, in a circumferential direction of rotational driving; a connecting section provided on a side wall of the first reserving cavity to suck the sample liquid by a capillary force and transfer the sample liquid to the operation cavity; and second reserving cavities that are disposed outside the operation cavity in the circumferential direction of the rotational driving and communicate with the outermost position of the operation cavity through a connecting passage. The connecting section is circumferentially extended farther than the liquid level of the sample liquid retained in the first reserving cavity.

United States patent application US 2009/0246082 discloses an analysis device comprising a separation chamber for separating a sample solution into a solution component and a solid component, a holding channel for holding a predetermined amount of the separated solid component, a mixing chamber connected to the holding channel, an overflow channel connected between the holding channel and the separation chamber, a sample overflow chamber into which the sample solution remaining in the separation chamber is discharged, and a joint channel connecting the separation chamber and the sample overflow chamber. After the separated solution component fills the overflow channel with priority by a capillary force, the separated solid component is transferred to the holding channel via the overflow channel, and a predetermined amount of the solid component is measured. The solid component in the holding channel is transferred to the mixing chamber by a centrifugal force, and simultaneously, the sample solution remaining in the separation chamber is discharged to the sample overflow chamber by the siphon effect of the joint channel.

SUMMARY

A method of performing a measurement, a cartridge for automatic analyzer, and an automatic analyzer are disclosed in the independent claims. Additional embodiments are given in the dependent claims. The measurement may be, for example, an optical measurement or an electrical measurement.

In one aspect the invention, an embodiment provides for a method of performing a measurement of a processed biological sample using a cartridge.

A cartridge as used here encompasses a test element for processing the biological sample into a processed biological sample. The cartridge may include structures or components which enable a measurement to be performed on the biological sample. A cartridge is a test element as is defined and explained in U.S. Pat. Nos. 8,114,351 B2 and 8,470,588 B2. A cartridge as used herein may also be referred to as a Centrifugal microfluidic disc, also known as "lab-on-a-disc" or a microfluidic CD.

A biological sample as used herein encompasses as chemical product derived, copied, replicated, or reproduced from a sample taken from an organism.

The cartridge comprises a fluid chamber for receiving a fluid. The cartridge further comprises an aliquoting chamber. The cartridge further comprises a duct connecting the fluid chamber and the aliquoting chamber. The duct is configured or is operable for transferring fluid from the fluid chamber to the aliquoting chamber. In some examples the aliquoting chamber is further away from the rotational axis than the fluid chamber is. In this case the duct may simply be a channel connecting the aliquoting chamber and the fluid chamber. In other examples the duct may be a siphon and may be used to transfer the fluid from the fluid chamber to the aliquoting chamber.

The cartridge further comprises a downstream fluidic element. The downstream fluidic element is considered to be fluidically downstream from the aliquoting chamber. The cartridge further comprises a siphon for siphoning the fluid from the aliquoting chamber to the downstream fluidic element. The siphon comprises a siphon entrance in the aliquoting chamber. The siphon further comprises a siphon exit in the downstream fluidic element. The siphon comprises a bend wherein the bend is the portion of the siphon closest to the rotational axis.

The siphon entrance starts at the bend but extends also to a lower portion of the aliquoting chamber. The lower portion is further from the rotational axis than the bend. The siphon entrance has a geometrical dimension which allows fluid to enter and fill the siphon by capillary action and is therefore functionally a part of the siphon structure. In contrast to the siphon part fluidically downstream of the siphon entrance, the siphon entrance extends into the aliquoting chamber. The aliquoting chamber has a minimum width adjacent to the siphon entrance. The siphon entrance has a siphon entrance width. Other portions of the siphon can have dimensions smaller than the siphon entrance width to improve capillary flow.

The siphon entrance width is less than the minimum width of the aliquoting chamber adjacent to the siphon entrance. The minimum width is simply the minimum width measured in the aliquoting chamber adjacent to the siphon entrance. For instance in many examples the cartridge is flat and disc-like and the various chambers and fluidic elements are constructed using planar shapes. However, this is not necessary; the aliquoting chamber for instance can have a varying width when measured in the axial direction. The minimum width adjacent to the siphon entrance is the minimum width of the aliquoting chamber adjacent to where the siphon entrance enters into the aliquoting chamber. There may be other portions of the aliquoting chamber adjacent to the siphon entrance that are larger; however, the minimum width is the smallest width of the aliquoting chamber adjacent to the siphon entrance. The minimum width of the aliquoting chamber is sufficiently large so that there is no capillary flow within the aliquoting chamber.

The cartridge further comprises a fluidic structure for processing a biological sample into the processed biological sample. The fluidic structure for processing a biological sample into the processed biological sample comprises or is fluidically connected to the downstream fluidic element. Fluidically connected as used herein encompasses a path, channel, or another fluidic connection which enables a fluid to be transported or transferred between two or more fluidic elements.

The downstream fluidic element is a fluidic element which is part of or fluidically connected to the fluidic structure for processing the biological sample into the processed biological sample. The fluidic structure comprises a measurement structure for enabling measurement of the processed biological sample. The fluidic structure is configured for receiving the biological sample.

The method comprises the step of placing the biological sample into the fluidic structure. There for instance may be a receptacle or a place for depositing the biological sample (e.g. a sample port). The method further comprises the step of controlling the rotational rate of the cartridge to process the biological sample into the processed biological sample using the fluidic structure. For instance the cartridge may be rotated around the rotational axis at various rates for different durations to perform the processing. The method further comprises filling the fluid chamber with the fluid. In some examples this may mean depositing fluid from an external source into the fluid chamber. In other examples a fluid reservoir which is within the fluid chamber or connected to it may be opened and thus fills the fluid chamber with the fluid.

The method further comprises the step of controlling the rotational rate of the cartridge to transport the fluid from the fluid chamber to the aliquoting chamber via the duct. For instance if the aliquoting chamber is further from the rotational axis than the fluid chamber then the cartridge can simply be rotated at a sufficiently large rate about the rotational axis and the centrifugal force will force the fluid radially outwards through the duct and into the aliquoting chamber. The method further comprises the step of controlling the rotational rate of the cartridge to transfer a first portion of the fluid from the aliquoting chamber to the downstream fluidic element. The siphon width of the siphon may be chosen such that the capillary action of the fluid in the siphon causes it to automatically be transferred from the aliquoting chamber into the siphon and to fill the siphon by capillary action. The passage between the siphon exit and the downstream fluidic element may be formed as a capillary stop valve such that the capillary forces in the siphon prevent the fluid to be transferred into downstream fluidic elements. Only if a centrifugal force is applied which exceeds the capillary force (and the surface tension) in the siphon the fluid can be transported into the radially outward located downstream fluidic element.

A capillary stop value as used herein is a valve or structure which uses the capillary force of a fluid to prevent fluid from flowing through the capillary stop valve. For example a tube with a sufficiently small diameter will draw fluid into it and the capillary force will prevent the fluid from flowing out of the tube. For the case of this tube the entrance and exit of the tube function as capillary stop valves. In some examples the siphon exit itself may have dimensions small enough (compared to the adjacent fluidic structures and chambers) that the siphon exit functions as a capillary stop.

Rotating the cartridge about the rotational axis at a sufficient rate will cause a centrifugal force that will counteract the capillary action of the siphon. Thus by rotating the cartridge at a sufficient rate the transfer of the fluid from the aliquoting chamber to the downstream fluidic element by the siphon can be prevented. Slowing the rotational rate allows the capillary action of the siphon to draw fluid into the siphon and to fill the siphon.

The method further comprises controlling the rotational rate of the cartridge to transfer the first portion of the fluid from the aliquoting chamber to the downstream fluidic element. The increase in the rotational rate of the cartridge causes air to enter the siphon at the bend. Normally when a siphon is transferring fluid it may only be used once. It should be noted that the air is able to enter the siphon directly at the bend because the siphon entrance extends all the way from the bend to the lower portion of the aliquoting chamber.

Having the bend exposed enables air to enter at this point. The increasing centrifugal force occurring from increasing the rotational rate of the cartridge acts on both "arms" of the siphon located radially outwards of the bend. The fluid contained in the siphon is transported radial outwards. The fluid portion which is contained in the siphon arm between the bend and the aliquoting chamber is transported back into the aliquoting chamber. The fluid portion which is contained within the siphon arm between the bend and the fluidic downstream element is transported into the downstream fluidic element. Because the bend exposed enables air to enter at the bend of the siphon air can enter into both arms of the siphon which separates the two fluid portions. The siphon will be cleared of fluid and may then be used again. This has an advantage of transferring a metered amount of fluid from the aliquoting chamber to the fluidic downstream element.

The method further comprises controlling the rotational rate of the cartridge to transfer at least a second portion of the fluid from the aliquoting chamber to the downstream fluidic element. In this step the rotational rate may be slowed again enabling the capillary action within the siphon to overcome the centrifugal force. This causes the siphon to be filled again with a second portion of the fluid from the aliquoting chamber. The method further comprises controlling the rotational rate of the cartridge to increase and to transfer the second portion of the fluid to the downstream fluidic element as described before. The increase in the rotational rate of the cartridge also causes again air to enter the siphon at the bend and to separate the two fluid portions contained in the respective arms of the siphon. This process can be repeated multiple times resulting in the subsequent transfer of multiple fluid portions in a controlled manner.

Because the volume of the siphon arm between the bend and the fluidic downstream element is defined this method can also be used to meter the fluid portion which is transported into the downstream fluidic element within each of the subsequent steps.

The method further comprises the step of performing the measurement using the measurement structure and using a measurement system. It should be noted that the first step of the method is placing the biological sample into the fluidic structure and the last step is performing the measurement. However, the other steps in the method may be performed in a different order and various steps may be performed more than once.

This method may have the advantage that the fluid can be transferred from the aliquoting chamber multiple times to the downstream fluidic element.

The patent application US 2009/0246082 A1 teaches the use of air holes which are positioned in various locations in an overflow chamber or channel. See for example FIGS. 3, 4, and 5 of US 2009/0246082 A1. The positioning of an air hole at the bend of a siphon however does not enable the repeatable aliquoting of fluid in the way that having a siphon entrance that extends from the bend to a lower portion of the aliquoting chamber. This advantage is described in greater detail below.

Similarly an aliquoting structure described in EP 2302396 A1 enables parallel splitting of fluid in several aliquots, but also uses a venting structure that only lets air in at the position nearest to the rotational axis. For example see FIG. 55 of EP 2302396 A1 and the accompanying text. The structure shown in the picture features a long capillary channel that has to be filled by fluid. The channel features several vents and connections to downstream chambers.

The structure shown in EP 2302396 has the following drawbacks: The refilling of such a structure for a second aliquoting step is highly unreliable. For a second aliquoting step the capillary has to be drained/emptied and thereafter filled again. As the walls of the capillary are still wet the filling process differs from the initial filling process of the first aliquoting step. The fluid moves significantly faster along the wetted channel walls than along the channels center. Due to the small channel diameter fluid progressing on one channel wall often gets in contact with fluid the opposing channel wall. This causes the formation of an air bubble that clogs the channel. This effect is significantly increased if fluids with low surface tension (e.g. washing buffers) are aliquoted. The probability of air bubble formation rises with the length of the capillary to be filled.

Experiments conducted show that long capillaries cannot be reliably used in repetitive aliquoting steps. A structure with a single long capillary and a vent near the bend was constructed. During the tests air bubbles clogged the vent consistently when a second aliquotation of the liquid is attempted. In contrast and according to our invention, having the siphon entrance extend from the bend to the lower portion of the aliquoting chamber provides a large area where air can be removed from the siphon into the aliquoting chamber. Further the capillary channel of the siphon entrance consists of three walls instead of four. Thereby the probability of fluid protruding along a siphon wall to get in contact with fluid protruding on the opposing siphon wall to form an air bubble is minimized. Both effects significantly reduce the probability that the siphon will be clogged by air bubbles.

The siphon with the siphon entrance extending from the bend to the lower portion of the aliquoting chamber enables serial aliquoting steps by reducing the length of the capillary to be filled in each aliquoting step. This siphon is split in two parts: The part leading radially inwards and a part of the bend at the radial inwards position feature for example only three channel walls. This part of the channel, which is the siphon entrance, is thereby connected over its whole length from the lower portion to the upper portion of the aliquoting chamber. In other words: The siphon entrance is open to the aliquoting chamber and is forming an "open" capillary structure with only three adjoining walls Such a channel with three walls, or with a channel entrance that extends from the bend to the lower portion of the aliquoting chamber, drastically reduces the probability for bubble formation. This increases the chances for refilling the capillary to perform serial aliquoting processes. The arm of the siphon leading radially outwards features four walls. Due to the fact that only this part of the capillary consists of four walls the length of the capillary in which bubble formation occurs with higher probability is reduced.

The above description assumes that the siphon has a rectangular or square profile. The above arguments apply mutatis mutandis to siphons with other profiles. For example the siphon could have a circular or oval profile with an open section along the wall that forms the siphon entrance.

In some examples the measurement is an optical measurement. The measurement may include, but is not limited to: a photometric transmission measurement, a measurement of the scattering of light, a chemiluminescence, fluorescence, a Total Internal Reflection Fluorescence (TIRF), and electrochemiluminescense (ECL) measurement.

In some examples the measurement structure may be or comprise a transparent structure.

In another embodiment the cartridge is horizontal when it is rotated. Placing the cartridge in a horizontal position is equivalent to placing the rotational axis in a vertical position.

In another embodiment the measurement structure is a transparent structure. The transparent structure may for example be a window. The transparent structure may also be optically transparent. In another example the transparent structure has more than one transparent and/or optical component. For example on one side one face of the container there may be a window and the other there may be a mirror. The optically transparent structure may for instance be a hole in one or both sides of the cartridge. The transparent structure may also comprise an optical filter. A transparent structure may also encompass being transparent outside of the visible range such as in the near infrared or near ultraviolet range. The optical measurement as used herein may also encompass measurements in the near infrared or near ultraviolet range. In other examples optically transparent may exclude the near infrared or near ultraviolet range.

In other examples the measurement structure comprises two or more electrodes for making an electrical measurement or ECL measurement of the processed biological sample. For example the measurement structures of Martinez-Duarte et. al. or Kim et. al. may be incorporated into a cartridge.

In other examples optically transparent may exclude the near infrared or near ultraviolet.

The fluidic structure may be a micro-fluidic structure.

It should be noted that processing the biological sample into the processed biological sample and the aliquoting of the fluid from the aliquoting chamber to the downstream fluidic element is not in any particular order and the aliquoting may take place multiple times during execution of the method.

In another aspect the invention provides for a cartridge for an automatic analyzer. The cartridge is operable for being spun around a rotational axis. The cartridge comprises a fluid chamber for receiving a fluid. The cartridge further comprises an aliquoting chamber. The cartridge further comprises a duct connecting the fluid chamber and the aliquoting chamber. The cartridge further comprises a downstream fluidic element. The cartridge further comprises a siphon for siphoning the fluid from the aliquoting chamber to the downstream fluidic element. The siphon comprises a siphon entrance in the aliquoting chamber. The siphon further comprises a siphon exit in the downstream fluidic element. The siphon comprises a bend. The bend is the portion of the siphon closest to the rotational axis. The siphon entrance starts at the bend. The siphon entrance extends to a lower portion of the aliquoting chamber. The lower portion is further from the rotational axis than the bend. The aliquoting chamber has a minimum width adjacent to the siphon. The siphon has a siphon width. The siphon width is less than the minimum width. The cartridge further comprises a fluidic structure for processing a biological sample into the processed biological sample. The fluidic structure further comprises the downstream fluidic element. The fluidic structure comprises a measurement structure for enabling the measurement of the processed biological sample. The fluidic structure is configured for receiving the biological sample. For instance the fluidic structure may have a receptacle or chamber into which the biological sample is placed.

In another embodiment the lower portion of the aliquoting chamber is a region or point of the aliquoting chamber that is furthest from the rotational axis.

In another embodiment the aliquoting chamber comprises a lowest point. The lowest point is the location of the aliquoting chamber furthest from the rotational axis. The siphon entrance extends to the lowest point. In this example the siphon entrance extends from the bend all the way to the lowest point of the aliquoting chamber. This may be beneficial because almost the complete fluid contained the aliquoting chamber can be transferred in multiple aliquotation steps to the downstream fluidic element. Only the fluid volume contained in the siphon arm between the bend and the siphon entrance cannot be transferred into the downstream fluidic element because this fluid volume will always be transferred back into the aliquoting chamber.

In some examples the radial width of the siphon entrance is greater than one half of the radial width of the aliquoting chamber. The radial width is the difference of two points measured to the rotational axis. The radial width of the aliquoting chamber is the radial width between the points of the aliquoting chamber closest and furthest away from the rotational axis. The radial width of the siphon entrance is radial width of the points of the siphon entrance closest and furthest from the rotational axis.

In another example the radial width of the siphon entrance is greater than one quarter of the radial width of the aliquoting chamber. In another example the radial width of the siphon entrance is greater than three quarters of the radial width of the aliquoting chamber.

In another embodiment the cartridge further comprises a reservoir filled with the fluid. The reservoir is configured for being opened and for transferring the fluid to the fluid chamber. The cartridge may have for example a reservoir opening element that could be used for opening the reservoir. It may also be possible that an actuator could be used to actuate or activate the reservoir opening element. For instance an automatic analyzer may have a device which would cause the actuation of the reservoir or a mechanism attached to it in order to open the reservoir allowing the fluid contained in the reservoir to be entered into the fluid chamber.

The reservoir may for example be sealed with a removable or pierceable seal that could for example be a thin film or a foil. For example a small piece of metal foil or a thin film of plastic may be used as a pierceable seal. The fluid chamber or another component of the cartridge may have a piercing structure for opening the pierceable seal. The piercing structure may be any structure which is capable of piercing the particular pierceable seal and for instance could be a pin, a lance, or a sharp edge. In other examples the removable seal may be able to be peeled off to open the reservoir.

In another embodiment the fluid chamber or a fluid receiving structure connected to the fluid chamber is configured for receiving a dosing needle for dispensing the fluid to the fluid chamber. This for instance may be performed manually or an automatic analyzer may have a dosing needle which automatically dispenses fluid to the fluid chamber or the fluid receiving structure.

In another embodiment the fluid is any one of the following: a dispersion, a fluid comprising nanoparticles, a fluid comprising a blood grouping reagent, a fluid comprising an immune reagent, a fluid comprising an antibody, a fluid comprising an enzyme, a fluid comprising one or more substrates for an enzymatic reaction, a fluid comprising fluorescence emitting molecules, a fluid comprising molecules for measuring immunochemical reactions, a fluid comprising molecules for measuring reactions of nucleic acids, a fluid comprising a recombinant protein, a fluid comprising virus isolate, a fluid comprising a virus, a fluid comprising a biological reagent, a solvent, a diluent, a buffer, a fluid comprising a protein, a fluid comprising a salt, a detergent, a fluid comprising a fluid comprising a nucleic acid, a fluid comprising an acid, a fluid comprising a base, an aqueous solution, a non-aqueous solution, and combinations thereof.

In another embodiment the siphon is operable for causing the fluid to enter and completely fill to the siphon by capillary action. This for instance may be selected by choosing the siphon width and also the other geometric dimensions of the siphon properly. This however is dependent also upon the particular composition and type of fluid, especially on its rheological characteristics In another embodiment the siphon width is between 100 µm and 500 µm. This may be beneficial because between 100 µm and 500 µm is a typical dimension where capillary action will allow the siphon to fill automatically.

In another embodiment the siphon exit is a capillary stop valve.

In another embodiment the measurement structure comprises two or more electrodes. The measurement structure is an electrode or an electrochemoluminescence system.

In another embodiment the measurement structure comprises a transparent structure. The measurement system comprises an optical measurement system.

Some examples may have both the measurement structure with the transparent structure and also the electrodes for more complicated tests. For example the measurement structure may be a structure for making electrochemiluminescence measurements: where electrodes cause an optical excitation in a sample.

Examples may also only have electrode. For example in an electrochemical detection structure an electrode may be used to measure a current caused by the result of an enzymatic reaction.

In another embodiment the aliquoting chamber comprises an upper portion. The upper portion is closer to the rotational axis than the lower portion. The upper portion contacts the bend. The siphon entrance opens into the upper portion and the lower portion. The upper portion has a first width. The first width is the width of the other portion adjacent to the siphon entrance. The lower portion has a second width. The second width is the width of the lower portion adjacent to the siphon entrance. The second width is greater than the first width. The siphon width is less than the first width.

In another embodiment the cartridge further comprises an excess fluid container connected to the aliquoting chamber. In some examples the excess fluid chamber may be connected to the lower portion of the aliquoting chamber. This may be used to control the total amount of fluid which goes into the aliquoting chamber and which can be transferred into the downstream fluidic chamber.

In another embodiment the aliquoting chamber comprises an atmospheric vent or vent. This may enable or assist the multiple aliquotation steps in the aliquoting chamber. In some embodiments the vent is in the upper portion.

In another embodiment the siphon comprises an air vent channel. An air vent channel as used herein encompasses a small channel or a channel which is adjacent to the siphon and connected along the length of the siphon for transporting air and/or and air bubble from one portion of the siphon to another portion of the siphon.

In one example the air vent channel is has a characteristic dimension or width that is smaller than the main channel of the siphon. The main channel is for transporting fluid. For example it was previously mentioned that the siphon may be between 100 μm and 500 μm in diameter or for the siphon width. In this example, the air vent channel attached along the siphon will have a characteristic dimension that is smaller than this. The siphon will then have an air vent channel with a width or diameter of approximately 80-400 μm.

In another example the air vent channel has a characteristic dimension or that is the same size or larger than a main channel of the siphon.

This extra channel or air vent channel next to the siphon may be advantageous if the siphon can clear itself of fluid and to enable re-usage of the siphon if more than one aliquotation is required.

In another aspect the invention provides for an automatic analyzer configured for receiving a cartridge according to an embodiment. The automatic analyzer comprises a cartridge spinner, a measurement system and a controller configured to control the automatic analyzer. In some examples the automatic analyzer may also have a dosing needle for dispensing fluid to the cartridge or it may also have an actuator for opening a reservoir filled with fluid that is connected to the fluid chamber. In some examples an operator would first put the biological sample into the cartridge and then install it into the automatic analyzer. In other examples the automatic analyzer may have a dosing needle which may allow to automatically put the biological sample into the cartridge or also to fill the fluid chamber with the fluid. The automatic analyzer may comprise a fluid filling means for filling the chamber with the fluid. The fluid filling means may either provide fluid via a dosing needle or open a reservoir using an actuator as described above.

The controller is configured or programmed to control the rotational rate of the cartridge to process the biological sample into the processed biological sample using the fluidic structure by controlling the cartridge spinner. The controller may be further configured or programmed to fill the fluid chamber with the fluid. This for instance may be achieved by controlling a dosing needle system or by manipulating an actuator which causes the reservoir to drain its fluid into the fluid chamber. The controller is further configured or programmed to control the rotational rate of the cartridge to transport the fluid from the fluid chamber to the aliquoting chamber via the duct by controlling the cartridge spinner. The controller is further configured for controlling the rotational rate of the cartridge to fill the siphon with the fluid a first time. The controller is further configured or programmed to control the rotational rate of the cartridge to increase to transfer a first portion of the fluid in the siphon to the downstream fluidic element by controlling the cartridge spinner. The increase in the rotational rate of the cartridge causes air to enter the siphon at the bend. The increase also forces the first portion of the fluid through the siphon exit. In some examples the siphon exit may function as a capillary stop valve. The controller is further configured or programmed to control the rotational rate of the cartridge to fill the siphon with fluid from the aliquoting chamber a second time. This is achieved by the controller controlling the cartridge spinner, and for example decreasing the rotational rate. The controller is further configured or programmed to control the rotational rate of the cartridge to increase to transfer a second portion of the fluid from the siphon to the downstream fluidic element. The increase in the rotational rate of the cartridge causes air to enter the siphon at the bend. The increase in the rotational rate also forces the second portion of the fluid through the siphon exit. Finally, the controller is further configured or programmed to perform the measurement using the measurement structure and the measurement system.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which:

FIG. 2 illustrates a portion of a method of making multiple aliquots of a fluid using the cartridge of FIG. 1;

FIG. 3 further illustrates a portion of a method of making multiple aliquots of a fluid using the cartridge of FIG. 1;

FIG. 13 shows a top an cross sectional view of the siphon of FIG. 11;

DETAILED DESCRIPTION

Figure 1:
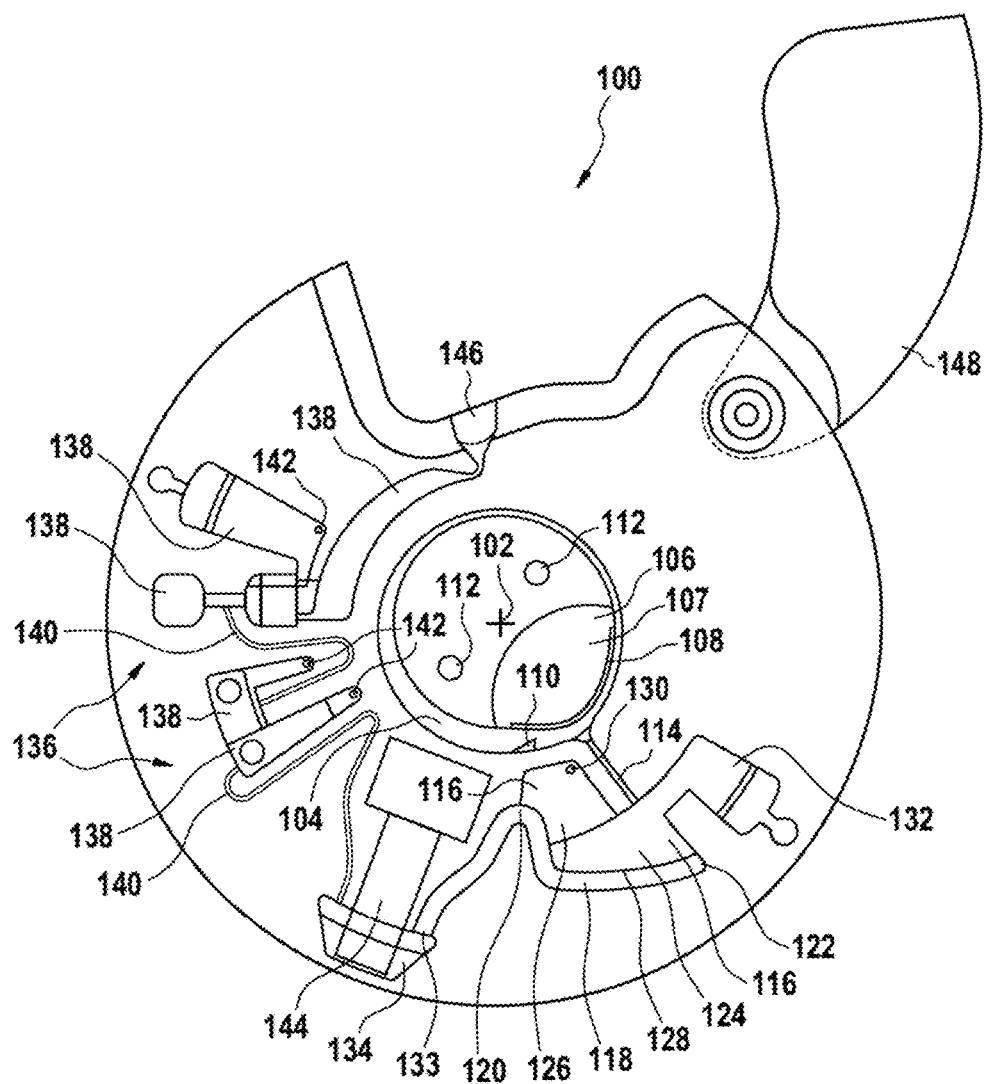
FIG. 1 illustrates an example of a cartridge.

Like numbered elements in these figures are either equivalent elements or perform the same function. Elements which have been discussed previously will not necessarily be discussed in later figures if the function is equivalent.

For heterogeneous immunochemical assays a washing buffer is often required to perform separation or washing steps to increase test sensitivity and reproducibility. For clinical chemistry tests buffers are often required for sample dilution or biochemical reactions. According to Richtlinie der Bundesärztekammer (RiliBÄK) guidelines for Point of Care (POC) disposables all liquid reagents have to be pre-stored on the disposable. From such pre-storage containers, the released fluid volume is typically released at once. If the fluid volume has to be split into aliquots complicated space-consuming microfluidic structures are required. This space consumption often hinders the implementation of parallel microfluidic structure for panels into microfluidic disposables.

Further, valves typically used for disc format disposables like siphons, geometrical valves or hydrophobic valves can either be used one time only or special variants of siphons can be used several times but a fluid volume in the interconnected chamber is completely transferred through the valve without the possibility to split the volumes into aliquots. Therefore with state-of-the art valves it is not possible to release a fluid volume from a pre-storage containment into a microfluidic cavity featuring a siphon valve and split this volume into several aliquots.

A disadvantage with geometrical valves is that there is no control of fluids with decreased surface tension is possible. This is especially true for washing buffers.

A disadvantage with using hydrophobic valves is that there no control of fluids with decreased surface tension is possible. This is especially true for washing buffers. Hydrophobic valves also have the disadvantage that they can only be used once.

A disadvantage of state of the art siphons is that state of the art siphons can only be filled once. Air bubbles remaining in the siphon after this has been used inhibit a second filling of the siphon. Further the siphons will transfer the complete fluid volume located radially inwards of the siphon from an aliquoting chamber into a downstream fluidic element. The aliquoting chamber may also be referred to as an upstream chamber.

Examples may have the advantage that air or an air bubble from vent in the bend of a siphon splits this fluid in the siphon into two parts. Each part has a defined volume. One part is transferred to the downstream fluidic element another part is transferred to the upstream chamber. The vent is not connected to the siphon via a narrow channel like in the state-of-the art systems. Instead the vent is in contact all along the complete rising arm of the siphon which is directed radially inwards to the siphon. The rising arm of the siphon is the portion of the siphon in contact with the aliquoting chamber and is between the bend and the furthest point of the siphon from the rotational axis. No wall separates the vent from the siphon. Therefore air bubbles occurring in the siphon can optimally be transferred into the vent. This may enable refilling of the siphon vent.

FIG. 1 shows an example of a cartridge 100. The cartridge is flat and disc-like and is shown as having a rotational axis 102. There is a fluid chamber 104 which is adapted or operable for receiving a fluid. The fluid reservoir 106 filled with a fluid 107 is sealed with a pierceable seal 108 in this example and there is a piercing element 110 on the wall of the fluid chamber 104. The fluid reservoir has a number of engaging surfaces or reservoir opening elements 112 which may be manipulated manually or by an apparatus such as an actuator which causes the pierceable seal 108 to contact the piercing element 110. This then causes the fluid chamber 104 to fill with the fluid 107. The fluid chamber 104 is shown as being connected to a duct 114. The duct 114 is connected to an aliquoting chamber 116. When the disc 100 is rotated about the rotational axis 102 centrifugal force forces fluid 107 through the duct 114. This then causes the aliquoting chamber 116 to fill with the fluid 107.

The aliquoting chamber 116 is shown as being connected to a siphon 118. There is a boundary 128 between the siphon 118 and the aliquoting chamber 116. This is a siphon entrance. The siphon 118 comprises a bend-like structure 120 which is the portion of the siphon 118 closest to the rotational axis 102. The siphon 118 is open to the aliquoting chamber 116 all along the boundary 128. In this example the siphon 118 can be seen as being extended all the way from the bend to a lowest point 122 of the aliquoting chamber 116. The lowest point 122 is the point of the aliquoting chamber 116 that is furthest from the rotational axis 102. This is however just an example. The siphon 118 could be designed differently such that the siphon does not extend all the way to the lowest point 122. In this case during use there may be some fluid 107 which remains within the aliquoting chamber 116. In this example the aliquoting chamber 116 is shown as having a lower portion 124 and an upper portion 126. In this example the aliquoting chamber 116 is laid out in a plane-like fashion aligned with the plane of the disc. The rotational axis is perpendicular to the plane. The upper portion 126 and the lower portion 124 may have different widths when measured along the axis of rotation 102. There is a vent 130 in an upper portion of the aliquoting chamber 116. Attached to the aliquoting chamber 116 is an excess fluid container 132. This is an optional element.

The siphon 118 is shown as having a siphon exit 133 into a downstream fluidic element 134. The siphon exit 133 may function as a capillary stop valve. The downstream fluidic element 134 is part of a fluidic structure 136 for processing a biological sample into a processed biological sample. The siphon 118 will have a characteristic width or diameter. The characteristic width or diameter of the siphon 118 will be less than the width of the aliquoting chamber 116 along the boundary 128. The fluidic structure 136 comprises a number of fluidic elements 138 that are connected by various ducts and siphons 140. There are also a number of vents 142 within the fluidic structure 136. In this example there is an opening 146 which enables a biological sample to be placed into the fluidic structure 136. There is also a cover lid 148 which is used to close and seal the opening 146. The fluidic structure 136 also comprises a measurement structure 144 which allows a measurement to be made on the biological sample using a measurement system.

The measurement system may for instance be an optical, electrical, or a combination of the two systems for making the measurement on the processed biological sample.

The processing of the biological sample can be controlled by controlling the rotational rate about the rotational axis and duration. The siphons 118, 140 are designed to be filled automatically using a capillary action. However, a sufficiently large rotational rate about the rotational axis 102 will produce a centrifugal force which will oppose the capillary action. Thus, by controlling the rotational rate and the duration of rotation at particular rates the processing of the biological sample and also the flow of fluid from the aliquoting chamber 116 to the downstream fluidic element 134 can be controlled. In a typical usage the biological sample may be placed into the inlet 146 and the rotation rate of the system may be controlled. Then at some point an actuator or other mechanical means is used to manipulate the reservoir opening element and causes the piercing element 110 to pierce the pierceable seal 108. Rotation can then force fluid into the aliquoting chamber and a variety of rotational rates may be used to perform multiple aliquotations using the cartridge 100.

FIGS. 2-8 are used to demonstrate how the aliquoting chamber 116 can be used to provide multiple aliquots of the fluid 107. In this example the cover lid 148 is drawn as being open. However, when the cartridge is being rotated about the rotational axis 102 the cover lid 148 would be closed.

Also in FIGS. 2-8 the pierceable seal 108 is shown as not having been ruptured. In reality the seal would have been ruptured.

FIG. 2 illustrates the start of the aliquoting process. The fluid 107 has been drained into the aliquoting chamber 116. The fluid 107 is shown as filling a portion of the aliquoting chamber 116 and the siphon 118. The disc 100 is rotating at a large enough rate about the rotational axis 102 that the centrifugal force is balancing the capillary action in the siphon 118 and the fluid 107 remains in the aliquoting chamber 116 and the radially outwards portions of the siphon 118 nearby the aliquoting chamber 116. The fluid 107 for instance may be a washing buffer or reagents from the fluid reservoir 106.

Next in FIG. 3 the rotational rate of the cartridge slows and the fluid 107 can be seen moving through the siphon 118 to the downstream fluidic element 134. The fluid 107 does not enter the downstream fluidic element 134 because the siphon exit 133 functions as a capillary valve preventing the fluid 107 from entering into the downstream fluidic chamber 136 without any additional force.

Figure 4:
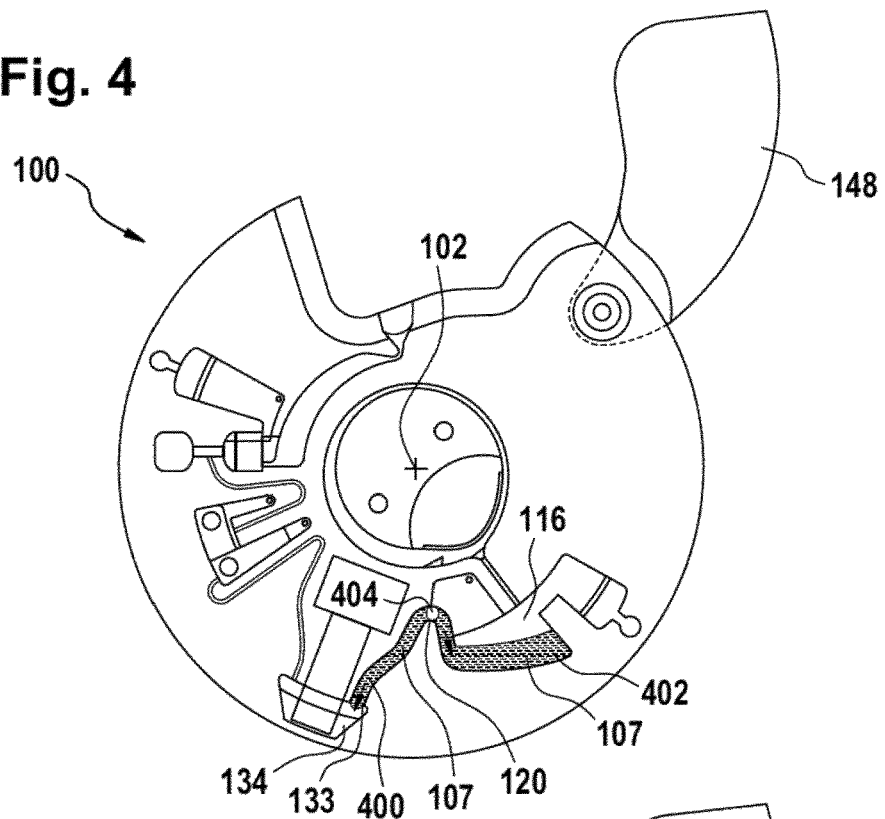
FIG. 4 further illustrates a portion of a method of making multiple aliquots of a fluid using the cartridge of FIG. 1.

In FIG. 4 the rotational rate about the rotational axis 102 is increased and the cartridge spins at a higher rate. This causes an increasing centrifugal force which overcomes the capillary forces at the capillary valve between the siphon 118 and the downstream chamber 134 allowing the fluid to enter the downstream fluidic chamber 134 now. As fluid is transferred from the siphon into the downstream fluidic chamber 134 (and also back to the aliquoting chamber 116), a bubble or amount of air 404 enters at the bend 120. The bend 120 is open to the aliquoting chamber 116 so air is able to be forced in at this point. In other words, the entrance for the siphon extends all the way from the bend to the lower portion of the aliquoting chamber. Because the bend is exposed to air in the aliquoting chamber this enables a bubble to form exactly at the bend and this enables the fluid to be split into two portions.

The centrifugal force then divides the fluid 107 into a first portion 400 of fluid and a remaining portion 402. The centrifugal force then transports the first portion 400 into the downstream fluidic element 134, through the siphon exit 133 and the remaining portion 402 back into the aliquoting chamber 116.

Figure 5:
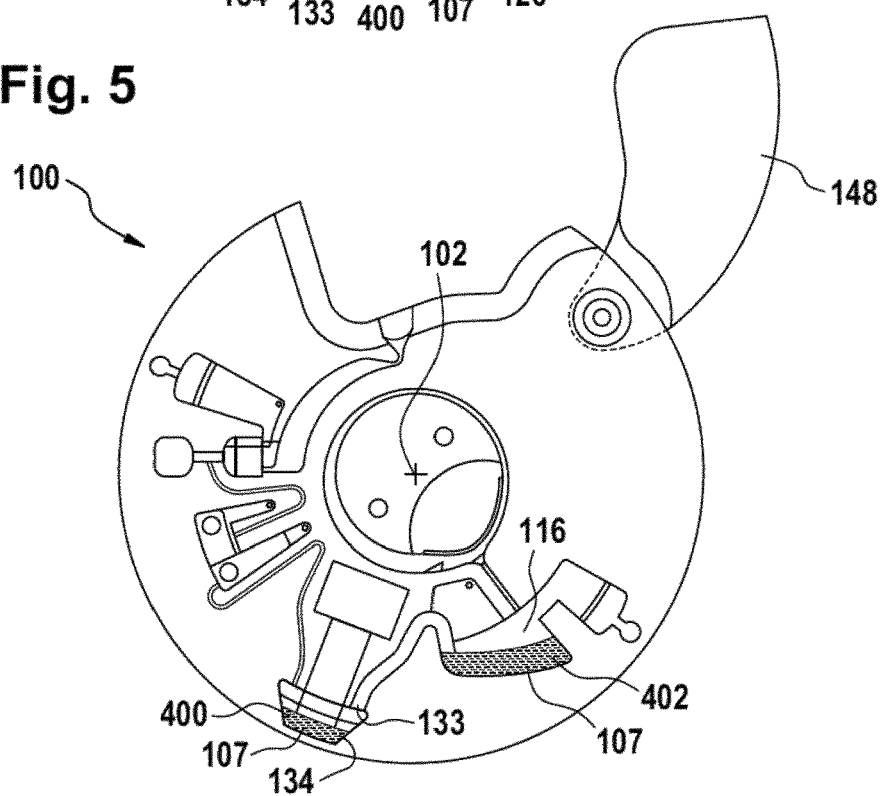
FIG. 5 further illustrates a portion of a method of making multiple aliquots of a fluid using the cartridge of FIG. 1.

FIG. 5 shows the cartridge 100 after the centrifugal force has pushed the first portion of the fluid 400 into the downstream fluidic element 134 and the remaining portion 402 into the aliquoting chamber 116.

Figure 6:
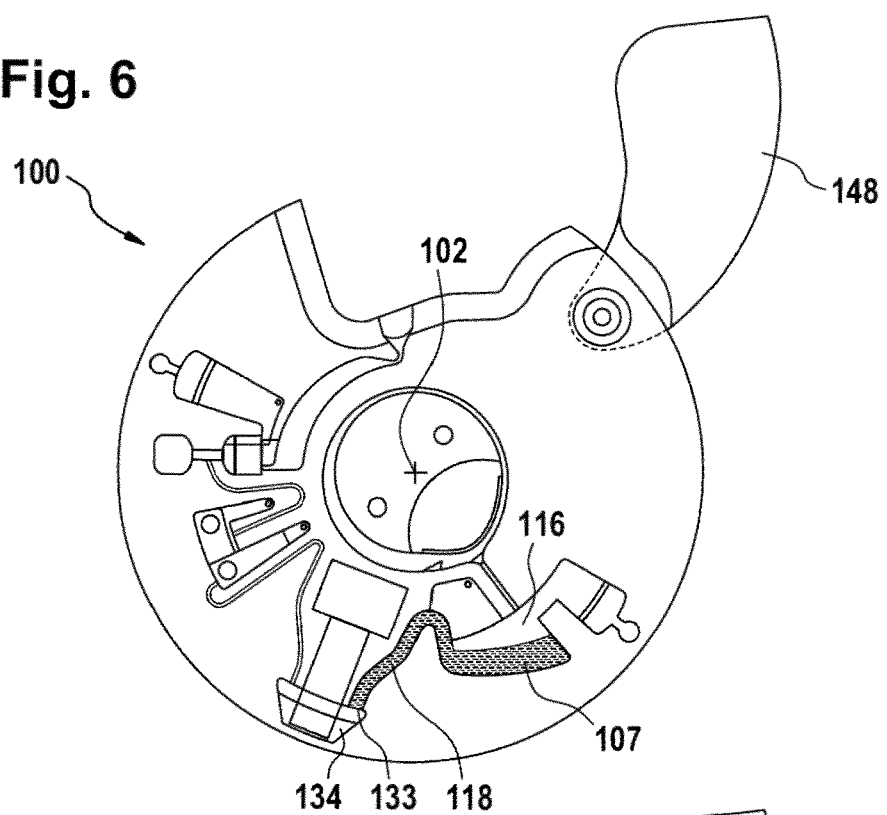
FIG. 6 further illustrates a portion of a method of making multiple aliquots of a fluid using the cartridge of FIG. 1.
Figure 7:
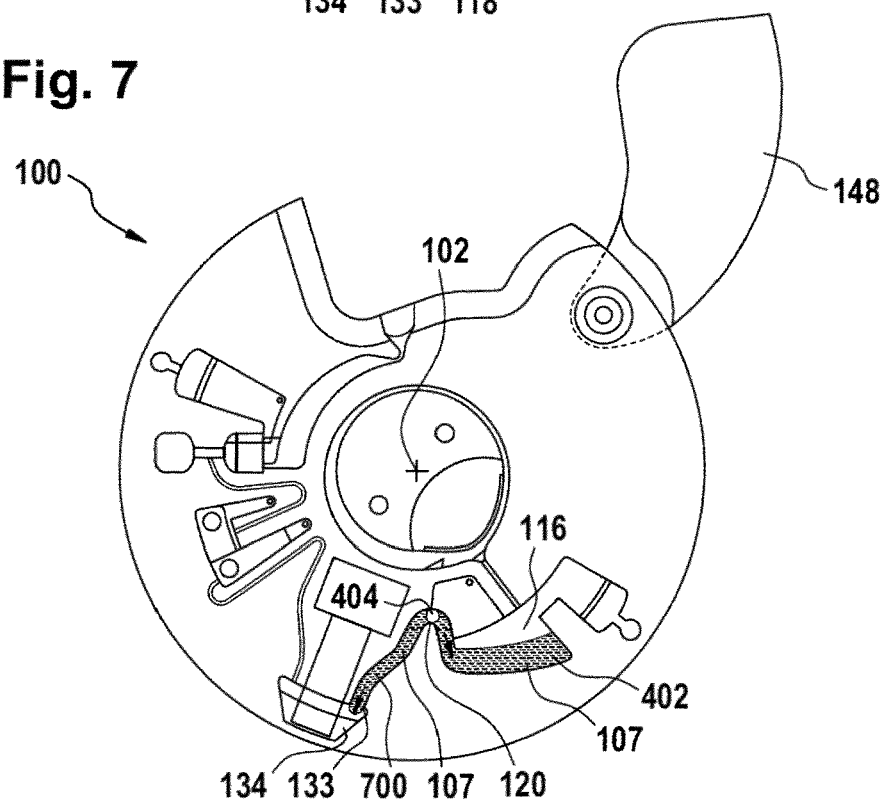
FIG. 7 further illustrates a portion of a method of making multiple aliquots of a fluid using the cartridge of FIG. 1.
Figure 8:
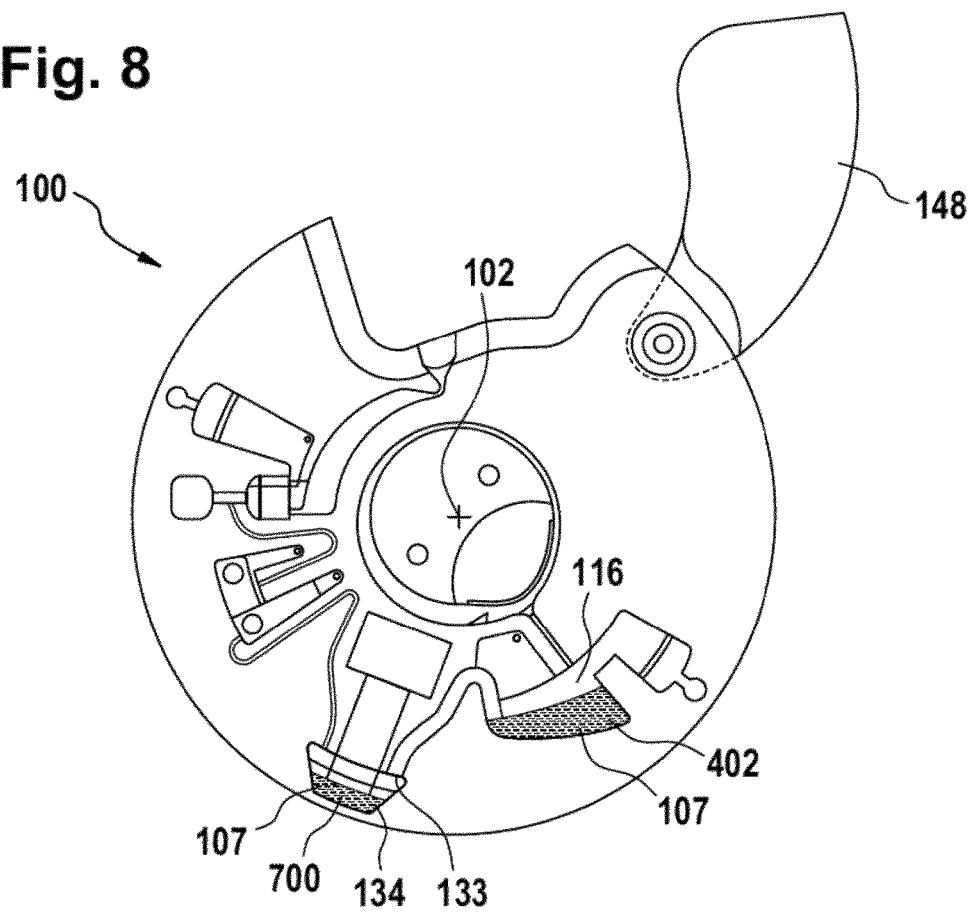
FIG. 8 further illustrates a portion of a method of making multiple aliquots of a fluid using the cartridge of FIG. 1.

FIGS. 6, 7 and 8 illustrate how this process may be repeated. After the first portion of fluid 400 is consumed or used next in FIG. 6 the rotational rate of the cartridge 100 is slowed. The capillary action again then forces the fluid 107 to flow into and fill the siphon 118 as was previously illustrated in FIG. 3. To transfer a further portion of the fluid into the downstream fluidic chamber 134 the rotational rate about the rotational axis 102 is then increased again such that the centrifugal force divides the fluid and the siphon 118 into two portions a second portion 700 and a remaining portion 402. This dividing of the fluid in the siphon was illustrated previously in FIG. 4. Performing a second aliquotation is illustrated in FIG. 7. This process may be repeated as long as there is fluid 107 in the aliquoting chamber 116.

After the fluid 700, 402 has been divided they look as they do in FIG. 8. This shows a repeat of the process shown in FIG. 5.

Figure 9:
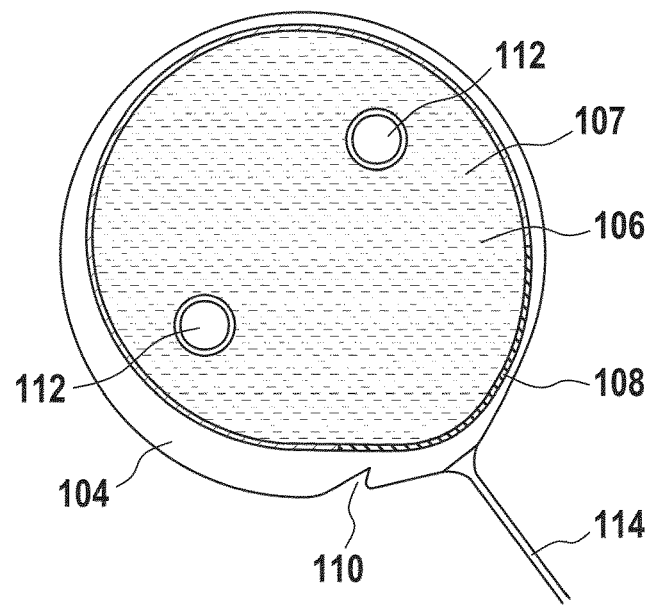
FIG. 9 illustrates an example of a fluid reservoir within a fluid chamber.

FIG. 9 shows the fluid reservoir 106 and fluid chamber 104 of FIG. 1 in greater detail.

Figure 10:
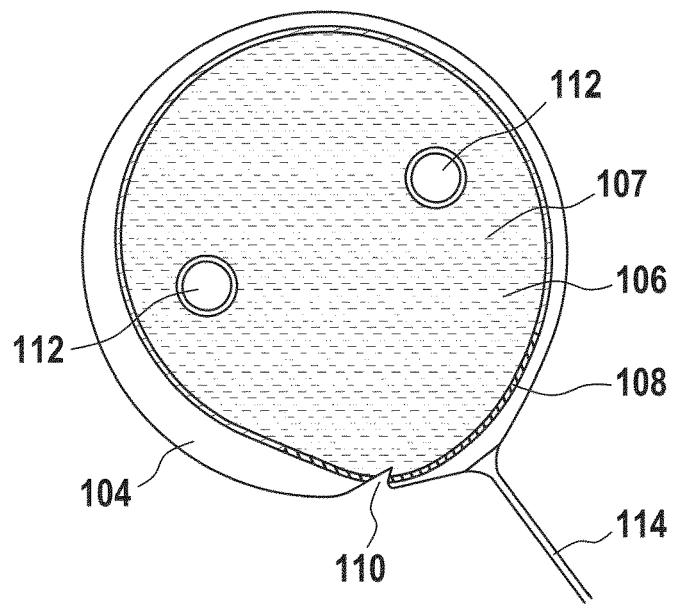
FIG. 10 illustrates the fluid reservoir of FIG. 9 being opened.

FIG. 10 shows the same view as FIG. 9 except the engaging surface or reservoir open element 112 has been actuated such that the pierceable seal 108 has been forced against the piercing element 110. This will cause fluid to drain from the fluid reservoir 106.

Figure 11:
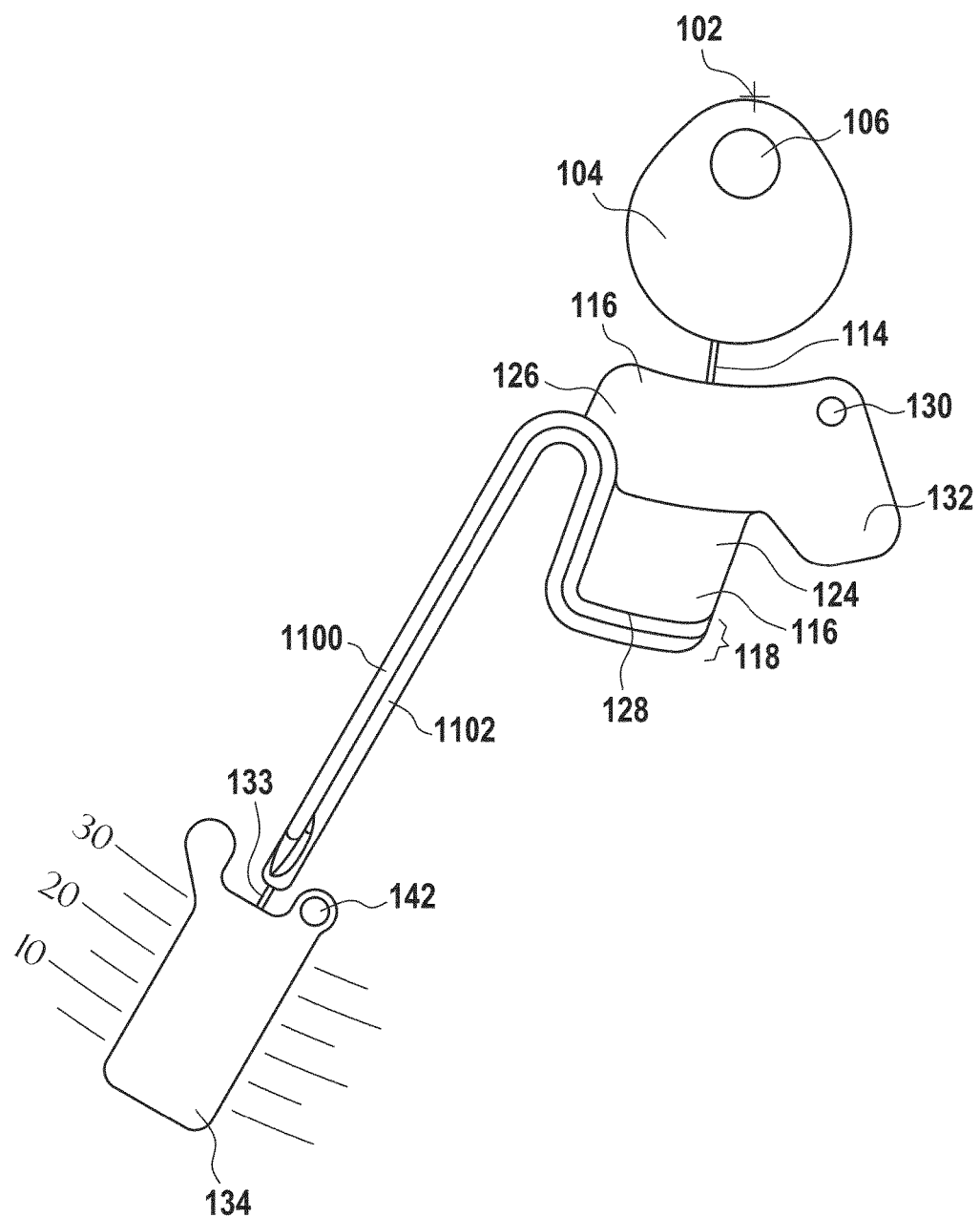
FIG. 11 shows a top view of a siphon between a aliquoting chamber and a downstream fluidic element.

FIG. 11 shows an aliquoting chamber 116, siphon 118 and downstream fluidic element 134 that is similar to that shown in FIG. 1. However, in this example the siphon 118 has a different design. The siphon 118 comprises two channels. There is a main siphon channel 1102 and an air vent channel 1100. The difference between this siphon 118 and the siphon shown in FIG. 1 is that the additional air vent channel 1100 provides a place for air to pass back through the siphon 118. This modified siphon 118 is designed such that air bubbles will not block the siphon 118. This facilitates the use of the aliquoting chamber 116 for making multiple aliquotations of the fluid 107. The view in FIG. 11 is a top view.

Figure 12:
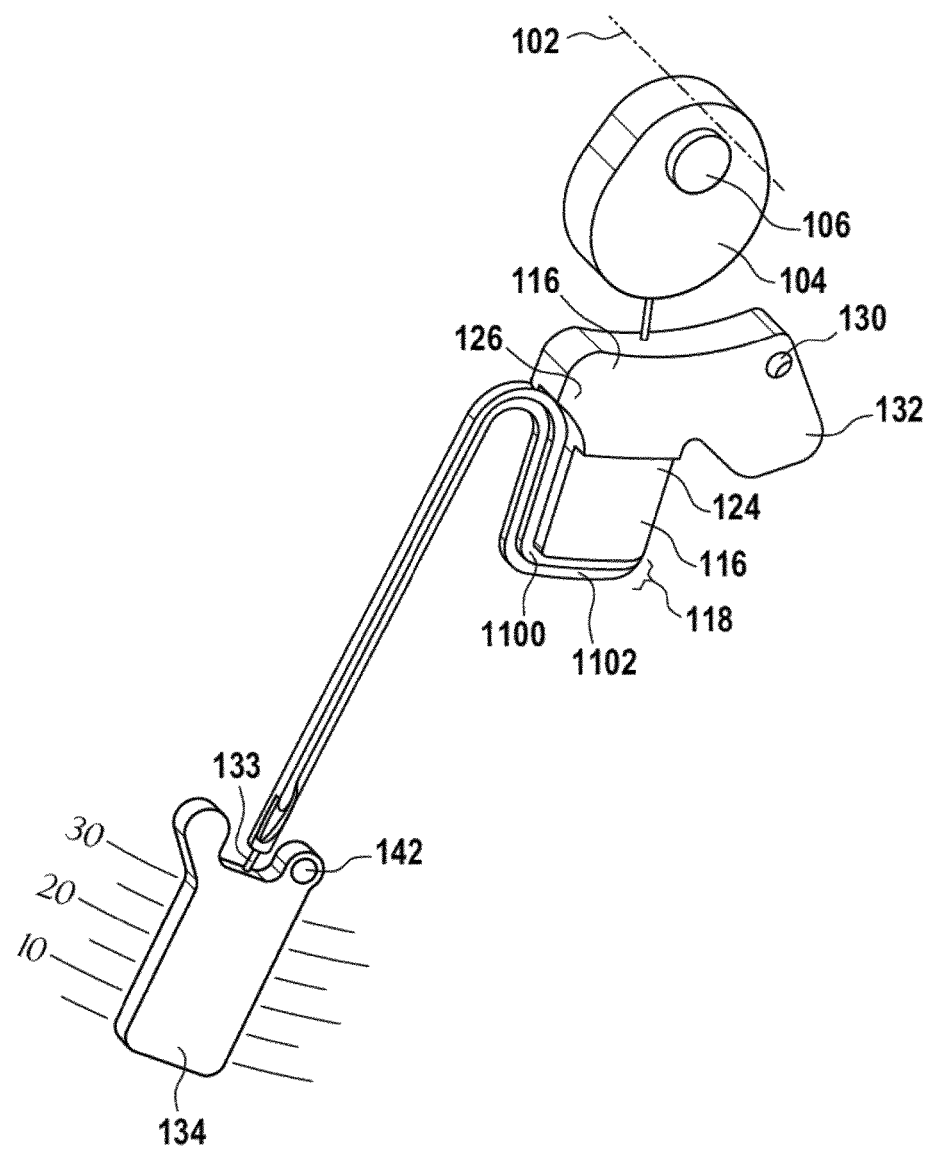
FIG. 12 shows a perspective view of the siphon of FIG. 11.

FIG. 12 shows the same structure as is shown in FIG. 11 except a perspective view is shown instead.

FIG. 13 shows the same view as is shown in FIG. 11. However, a first cross-sectional line AA labeled 1300 and a second cross-sectional line 1302 labeled BB has been drawn in. A first cross-sectional view across line A-A 1300 is shown in illustration 1304. The second cross-sectional view B-B is shown in cross-sectional view 1306. In these cross-sectional views the siphon channel 1102 and the air vent channel 1100 can be distinctly seen. In cross-sectional B-B the siphon 118 next to the aliquoting chamber 116 can be seen. Also in this Fig. the relative widths of the air vent channel 1310, the siphon width 1308 and the minimum width 1312 at the boundary 128 can also be seen.

Figure 14:
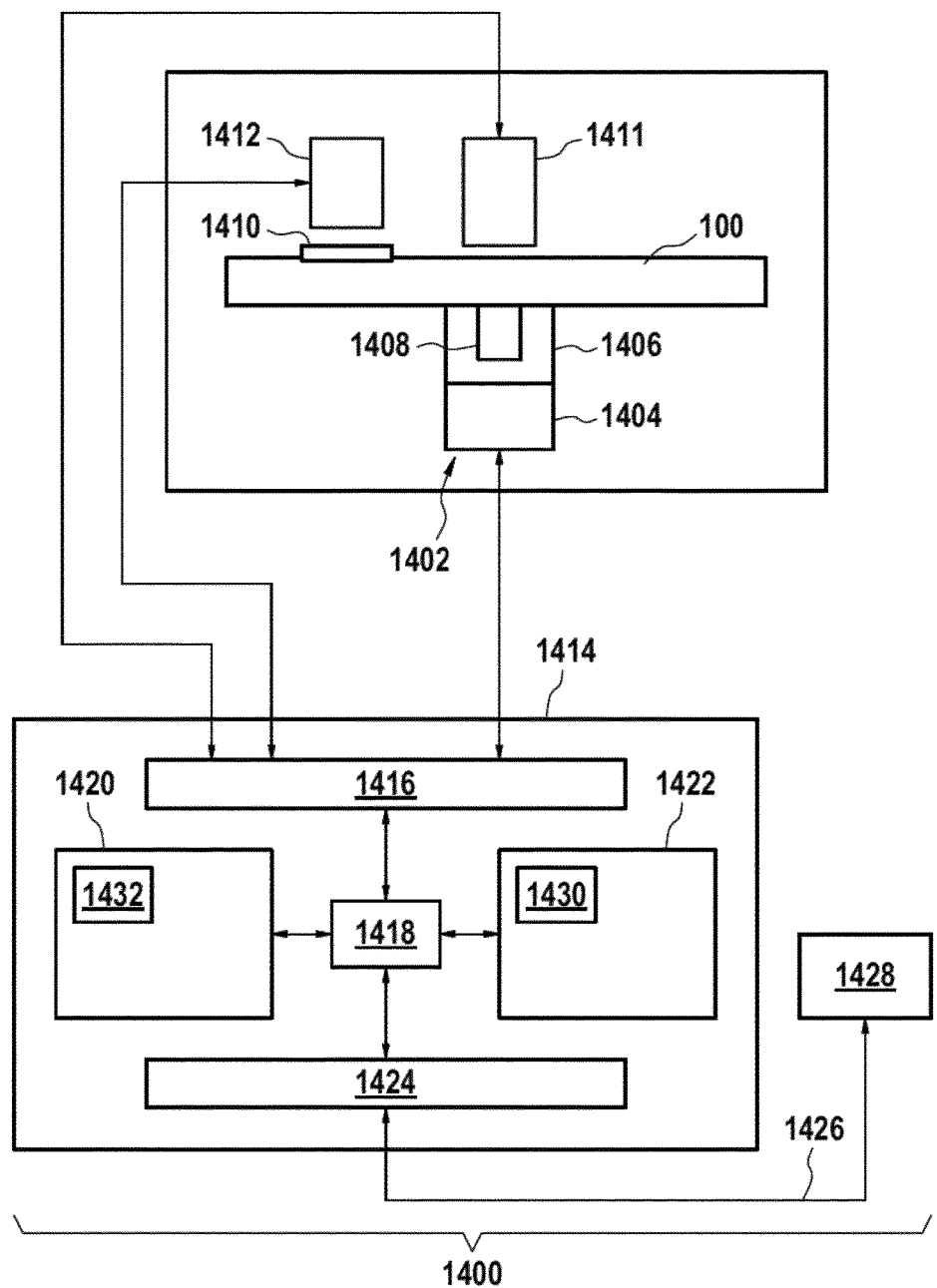
FIG. 14 illustrates an example of an automatic analyzer.

FIG. 14 shows an example of an automatic analyzer. The automatic analyzer 1400 is adapted for receiving a cartridge 100. There is a cartridge spinner 1400 which is operable for rotating the cartridge 100 about the rotational axis 102. The cartridge spinner 1402 has a motor 1404 attached to a gripper 1406 which attaches to a portion of the cartridge 1408. The cartridge 100 is shown further as having a measurement or transparent structure 1410. The cartridge 100 can be rotated such that the measurement structure 1410 goes in front of a measurement system 1412 which can perform for example an optical measurement on the processed biological sample. The actuator 1404 as was shown previously is also shown in this figure. It can be used to open a fluid reservoir(s) in the cartridge 100. In some examples the actuator may be replaced with a dispenser with a dosing needle for filling the fluid chamber of the cartridge 100.

The actuator 1411, the cartridge spinner 1402, and the measurement system 1412 are shown as all being connected to a hardware interface 1416 of a controller 1414. The controller 1414 contains a processor 1418 in communication with the hardware interface 1416, electronic storage 1420, electronic memory 1422, and a network interface 1424. The electronic memory 1430 has machine executable instructions which enable the processor 1418 to control the operation and function of the automatic analyzer 1400. The electronic storage 1420 is shown as containing a measurement 1432 that was acquired when instructions 1430 were executed by the processor 1418. The network interface 1424 enables the processor 1418 to send the measurement 1432 via network interface 1426 to a laboratory information system 1428.

Figure 15:
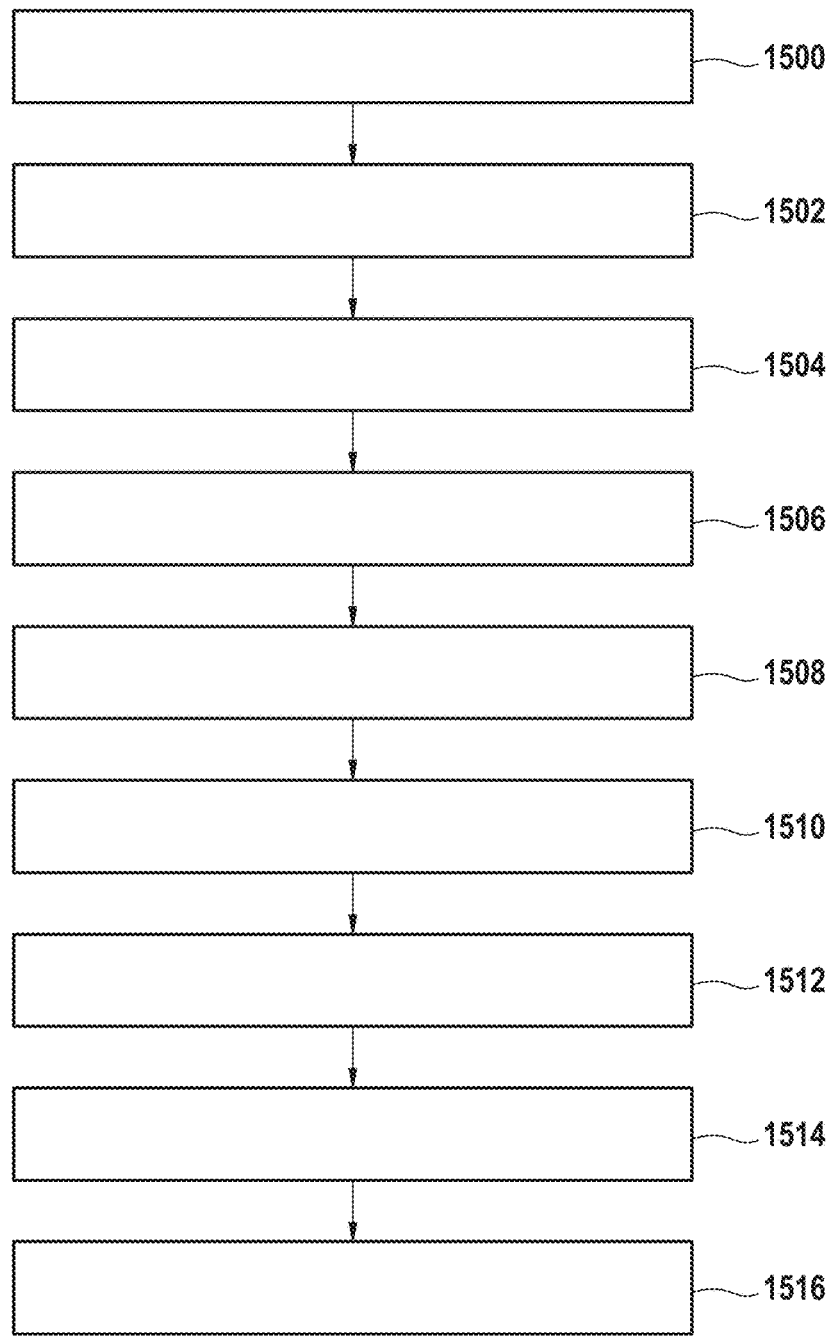
FIG. 15 shows a flow chart which illustrates a method of operating the automatic analyzer of FIG. 14.

FIG. 15 shows a flowchart which illustrates a method of using or operating the automatic analyzer 1400 of FIG. 14. First in step 1500 the biological sample is placed into the fluidic structure. For example when using the cartridge 100 this may include adding a fluid or other biological sample into the opening 146 and then closing the cover 148. Next in step 1502 the processor 1418 controls the motor 1404 to rotate the cartridge 100 at varying rotational rates for differing times to process the biological sample into the processed biological sample using the fluidic structure 136. Next in step 1504 the fluid chamber 104 is filled with the fluid 107. This may be done by inserting a dosing needle into a specially designed fluid chamber or receptacle for the fluid chamber or it may be done as is illustrated in FIG. 1 by opening a reservoir 106 that is within or is connected to the fluid chamber 104.

Next in step 1506 the processor controls the motor 1404 to control the rotational rate of the cartridge to transport the fluid from the fluid chamber to the aliquoting chamber via the duct. The rotation of the cartridge 100 causes centrifugal force which causes the fluid to pass through the duct 114 into the aliquotation chamber. Next in step 1508 the processor 1418 again controls the rotational rate of the cartridge by controlling the motor 1404. This may include reducing the rotational rate of the cartridge or even stopping the rotation of the cartridge altogether with the rotational force acting on the fluid within the aliquoting chamber 116. This causes the siphon 118 to fill with the fluid a first time. Next in step 1510 the processor 1418 controls the motor 1404 such that the rotational rate of the cartridge increases. This causes the first portion of the fluid, the fluid between the siphon exit 133 and the bend 120, to enter into the downstream fluidic element 134. The increase in the rotational rate of the cartridge causes air to enter the siphon at the bend. The increase in the rotational rate also forces fluid through the siphon exit, which functions as a capillary stop valve.

Next in step 1512 the rotational rate of the cartridge is controlled to allow the siphon to fill with the fluid from the aliquoting chamber to the downstream fluidic element a second time. This many include reducing the rotational rate of the cartridge 100.

Next in step 1514 the processor 1418 controls the motor 1404 such that the rotational rate of the cartridge increases to transfer a second portion of the fluid from the siphon to the downstream fluidic element. The increase in the rotational rate of the cartridge causes the air to enter the siphon at the bend 120. The amount of fluid transferred to the downstream fluidic element 134 is defined by the volume of fluid in the siphon between the siphon exit 133 and the bend 120. These processes can be repeated over and over to controllably transfer a metered amount of fluid to the downstream fluidic element.

Finally in step 1516 the processor 1418 controls the measurement system 1412 to perform the measurement using the measurement structure 1410 using the measurement system 1412.

The method of FIG. 15 is comparable to FIGS. 2-8. FIG. 2 corresponds to step 1506. FIG. 3 corresponds to FIG. 1508. FIG. 4 and FIG. 5 correspond to step 1510. FIG. 6 corresponds to step 1512. FIGS. 7 and 8 correspond to step 1514.

LIST OF REFERENCE NUMERALS 100 cartridge
102 rotational axis
104 fluid chamber
106 fluid reservoir with fluid
107 fluid
108 pierceable seal
110 piercing element
112 engaging surface or reservoir opening element
114 duct
116 aliquoting chamber
118 siphon
120 bend
122 lowest point
124 lower portion
126 upper portion
128 boundary between siphon and aliquoting chamber
130 vent
132 excess fluid container
133 siphon exit
134 downstream fluidic element
136 fluidic structure
138 fluidic element
140 siphon
142 vent
144 measurement structure
146 opening
148 cover lid
400 first portion of fluid
402 remaining portion of fluid
404 air
700 second portion of fluid
1100 air vent channel
1102 main siphon channel
1300 first section line A-A
1302 second section line B-B
1304 cross sectional view at first section line
1306 cross sectional view at second section line
1308 siphon width
1310 air vent channel width
1312 minimum width at boundary 128
1400 automatic analyzer
1402 cartridge spinner
1404 motor
1406 gripper
1408 portion of cartridge
1410 measurement structure
1411 actuator
1412 measurement system
1414 controller
1416 hardware interface
1418 processor
1420 electronic storage
1422 electronic memory
1424 network interface
1426 network connection
1428 laboratory information system
1430 executable instructions
1432 measurement
1500 placing the biological sample into the fluidic structure;
1502 controlling the rotational rate of the cartridge to process the biological sample into the processed biological sample using the fluidic structure
1504 filling the fluid chamber with the fluid
1506 controlling the rotational rate of the cartridge to transport the fluid from the fluid chamber to the aliquoting chamber via the duct 1508 controlling the rotational rate of the cartridge to transfer a first portion of the fluid from the aliquoting chamber to the downstream fluidic element 1510 controlling the rotational rate of the cartridge to increase to halt transfer of the first portion of the fluid from the aliquoting chamber to the downstream fluidic element 1512 controlling the rotational rate of the cartridge to transfer at least a second portion of the fluid from the aliquoting chamber to the downstream fluidic element 1514 controlling the rotational rate of the cartridge to increase to halt transfer of the second portion of the fluid from the aliquoting chamber to the downstream fluidic element 1516 performing the measurement using the measurement structure and using a measurement system

What is claimed is:

1. A method of performing a measurement of a processed biological sample using a cartridge, wherein the cartridge is operable for being spun around a rotational axis, wherein the cartridge comprises:
a fluid chamber for receiving a fluid;
an aliquoting chamber;
a duct connecting the fluid chamber and the aliquoting chamber;
a downstream fluidic element;
a siphon for siphoning the fluid from the aliquoting chamber to the downstream fluidic element, wherein the siphon comprises a siphon entrance into the aliquoting chamber, wherein the siphon further comprises a siphon exit into the downstream fluidic element, wherein the siphon comprises a bend, wherein the bend is the portion of the siphon closest to the rotational axis, wherein the siphon entrance extends all the way from the bend to the lowest point of the aliquotinq chamber, the lowest point being located in a lower portion of the aliquoting chamber, wherein the lower portion is further from the rotational axis than the bend, wherein the aliquoting chamber has a minimum width adjacent to the siphon, wherein the siphon has a siphon width, wherein the siphon width is less than the minimum width of the aliquoting chamber in a cross-sectional view; and
a fluidic structure for processing a biological sample into the processed biological sample, wherein the fluidic structure comprises the downstream fluidic element, wherein the downstream fluidic element is fluidically connected to the fluidic structure, wherein the fluidic structure comprises a measurement structure for enabling measurement of the processed biological sample, wherein the fluidic structure is configured for receiving the biological sample;
wherein the method comprises the steps of:
placing the biological sample into the fluidic structure;
controlling the rotational rate of the cartridge to process the biological sample into the processed biological sample using the fluidic structure;
filling the fluid chamber with the fluid;
controlling the rotational rate of the cartridge to transport the fluid from the fluid chamber to the aliquoting chamber via the duct;
controlling the rotational rate of the cartridge to fill the siphon with the fluid a first time;
controlling the rotational rate of the cartridge to increase in order to transfer a first portion of the fluid in the siphon to the downstream fluidic element, wherein the increase in the rotational rate of the cartridge causes air to enter the siphon at the bend, wherein the increase in the rotational rate of the cartridge forces the first portion of the fluid through the siphon exit;
controlling the rotational rate of the cartridge to fill the siphon with the fluid a second time;
controlling the rotational rate of the cartridge to increase in order to transfer a second portion of the fluid in the siphon to the downstream fluidic element, wherein the increase in the rotational rate of the cartridge causes air to enter the siphon at the bend, wherein the increase in the rotational rate of the cartridge forces the second portion of the fluid through the siphon exit, wherein the first portion and the second portion have the same volume; and
performing the measurement using the measurement structure and using a measurement system.

2. The method of claim 1, wherein the cartridge further comprises a reservoir filled with the fluid, wherein the reservoir is configured for being opened and for transferring the fluid to the fluid chamber.

3. The method of claim 1, wherein the siphon is operable for causing fluid to flow to the downstream fluidic element using capillary action.

4. The method of claim 1, wherein the fluid is any one of the following: a dispersion, a fluid comprising nanoparticles, a fluid comprising a blood grouping reagent, a fluid comprising an immune reagent, a fluid comprising an antibody, a fluid comprising an enzyme, a fluid comprising one or more substrates for an enzymatic reaction, a fluid comprising fluorescence emitting molecules, a fluid comprising molecules for measuring immunochemical reactions, a fluid comprising molecules for measuring reactions of nucleic acids, a fluid comprising a recombinant protein, a fluid comprising virus isolate, a fluid comprising a virus, a fluid comprising a biological reagent, a solvent, a diluent, a buffer, a fluid comprising a protein, a fluid comprising a salt, a detergent, a fluid comprising a fluid comprising a nucleic acid, a fluid comprising an acid, a fluid comprising a base, an aqueous solution, a non-aqueous solution, and combinations thereof.

5. A cartridge for an automatic analyzer, wherein the cartridge is operable for being spun around a rotational axis, wherein the cartridge comprises:
a fluid chamber for receiving a fluid;
an aliquoting chamber;
a duct connecting the fluid chamber and the aliquoting chamber;
a downstream fluidic element;
a siphon for siphoning the fluid from the aliquoting chamber to the downstream fluidic element, wherein the siphon comprises a siphon entrance in the aliquoting chamber, wherein the siphon further comprises a siphon exit in the downstream fluidic element, wherein the siphon comprises a bend, wherein the bend is the portion of the siphon closest to the rotational axis, wherein the siphon entrance extends all the way from the bend to the lowest point of the aliquotinq chamber, the lowest point being located in a lower portion of the aliquoting chamber, wherein the lower portion is further from the rotational axis than the bend, wherein the aliquoting chamber has a minimum width adjacent to the siphon, wherein the siphon has a siphon width, wherein the siphon width is less than the minimum width of the aliquoting chamber in a cross-sectional view; and
a fluidic structure for processing a biological sample into the processed biological sample, wherein the fluidic structure comprises the downstream fluidic element, wherein the downstream fluidic element is fluidically connected to the fluidic structure, wherein the fluidic structure comprises a measurement structure for enabling measurement of the processed biological sample, wherein the fluidic structure is configured for receiving the biological sample.

6. The cartridge of claim 5, wherein the aliquoting chamber comprises a lowest point, wherein the lowest point is the location of the aliquoting chamber furthest from the rotational axis, wherein the siphon entrance extends to the lowest point.

7. The cartridge of claim 5, wherein the fluid chamber or a fluid receiving structure connected to the fluid chamber is configured for receiving a dosing needle for dispensing the fluid to the fluid chamber.

8. The cartridge of claim 5, wherein the siphon width is between 100 micrometers and 500 micrometers.

9. The cartridge of claim 5, wherein the measurement structure comprises two or more electrodes, and wherein the measurement system is an electrode or an electro chemo luminescence system.

10. The cartridge of claim 5, wherein measurement structure comprises a transparent structure, and wherein the measurement system is an optical measurement system.

11. The cartridge of claim 5, wherein the aliquoting chamber comprises an upper portion, wherein the upper portion is closer to the rotational axis than the lower portion, wherein the upper portion contacts the bend, wherein the siphon entrance opens into the upper portion and the lower portion, wherein the upper portion has a first width, wherein the first width is the width of the upper portion adjacent to the siphon entrance, wherein the lower portion has a second width, wherein the second width is the width of the lower portion adjacent to the siphon entrance, wherein the second width is greater than the first width, wherein the first width is the minimum width, and wherein the siphon width is less than the first width.

12. The cartridge of claim 5, wherein the cartridge further comprises an excess fluid container connected to the aliquoting chamber.

13. The cartridge of claim 5, wherein the aliquoting chamber comprises an atmospheric vent, the atmospheric vent being located in the upper portion of the aliquoting chamber.

14. The cartridge of claim 5, wherein the siphon comprises an air vent channel.

15. The cartridge of claim 14, wherein the width of the air vent channel is less than the siphon width.

16. Automatic analyzer configured for receiving a cartridge according to claim 5, wherein the automatic analyzer comprises a cartridge spinner, a measurement system, and a controller configured to control the automatic analyzer, wherein the controller is configured to:

controlling the rotational rate of the cartridge to process the biological sample into the processed biological sample using the fluidic structure by controlling the cartridge spinner;

filling the fluid chamber with the fluid;

controlling the rotational rate of the cartridge to transport the fluid from the fluid chamber to the aliquoting chamber via the duct by controlling the cartridge spinner;

controlling the rotational rate of the cartridge to fill the siphon with the fluid a first time;

controlling the rotational rate of the cartridge to increase in order to transfer the first portion of the fluid from the siphon to the downstream fluidic element, wherein the increase in the rotational rate of the cartridge causes air to enter the siphon at the bend by controlling the cartridge spinner, wherein the increase in the rotational rate of the cartridge forces the first portion of the fluid through the siphon exit;

controlling the rotational rate of the cartridge to fill the siphon with the fluid a second time;

controlling the rotational rate of the cartridge to increase in order to transfer a second portion of the fluid from the siphon to the downstream fluidic element, wherein the increase in the rotational rate of the cartridge causes air to enter the siphon at the bend by controlling the cartridge spinner, wherein the increase in the rotational rate of the cartridge forces the second portion of the fluid through the siphon exit, wherein the first portion and the second portion have the same volume; and performing the measurement using the measurement structure by controlling the measurement system.

* * * * *

UNITED STATES PATENT AND TRADEMARK OFFICE
CERTIFICATE OF CORRECTION

Page 1 of 1

PATENT NO. : 10,016,758 B2
APPLICATION NO. : 15/352689
DATED : July 10, 2018
INVENTOR(S) : Boehm et al.

It is certified that error appears in the above-identified patent and that said Letters Patent is hereby corrected as shown below:

In the Claims

Column 19, Line 35, Claim 1:
"the bend to the lowest point of the aliquotinq chamber,"
Should read:
--the bend to the lowest point of the aliquoting chamber,--; and Column 20, Line 37, Claim 4:
"a detergent, a fluid comprising a fluid comprising a nucleic"
Should read:
--a detergent, a fluid comprising a nucleic--.

Signed and Sealed this
Fourteenth Day of May, 2019

Andrei Iancu
*Director of the United States Patent and Trademark Office*